United States Patent
Browning et al.

(10) Patent No.: US 8,067,375 B2
(45) Date of Patent: Nov. 29, 2011

(54) TREATMENT OF DEMYELINATING DISORDERS WITH SOLUBLE LYMPHOTOXIN-β-RECEPTOR

(75) Inventors: Jeffrey L. Browning, Brookline, MA (US); Jenny P-Y Ting, Chapel Hill, NC (US)

(73) Assignees: Biogen Idec MA Inc., Cambridge, MA (US); University of North Carolina at Chapel Hill, Chapel Hill, NC (US)

( * ) Notice: Subject to any disclaimer, the term of this patent is extended or adjusted under 35 U.S.C. 154(b) by 143 days.

(21) Appl. No.: 12/446,041

(22) PCT Filed: Oct. 18, 2007

(86) PCT No.: PCT/US2007/081761
§ 371 (c)(1),
(2), (4) Date: Aug. 31, 2009

(87) PCT Pub. No.: WO2008/049053
PCT Pub. Date: Apr. 24, 2008

(65) Prior Publication Data
US 2010/0099608 A1    Apr. 22, 2010

Related U.S. Application Data

(60) Provisional application No. 60/862,343, filed on Oct. 20, 2006.

(51) Int. Cl.
*A61K 38/00* (2006.01)
*A61P 35/00* (2006.01)
*C07K 1/00* (2006.01)
*C07K 14/00* (2006.01)
*C07K 17/00* (2006.01)

(52) U.S. Cl. .......... 514/19.2; 514/1.1; 530/351

(58) Field of Classification Search .......... None
See application file for complete search history.

(56) References Cited

U.S. PATENT DOCUMENTS

| | | | |
|---|---|---|---|
| 3,773,919 A | 11/1973 | Boswell et al. | |
| 4,338,397 A | 7/1982 | Gilbert et al. | |
| 4,485,045 A | 11/1984 | Regen | |
| 4,544,545 A | 10/1985 | Ryan et al. | |
| 4,758,549 A | 7/1988 | Mitsuhashi et al. | |
| 4,816,567 A | 3/1989 | Cabilly et al. | |
| 4,822,605 A | 4/1989 | Powell | |
| 4,849,509 A | 7/1989 | Thurin et al. | |
| 4,959,457 A | 9/1990 | Bringman | |
| 5,082,783 A | 1/1992 | Ernst et al. | |
| 5,225,538 A | 7/1993 | Capon et al. | |
| 5,447,851 A | 9/1995 | Beutler et al. | |
| 5,541,087 A | 7/1996 | Lo et al. | |
| 5,605,690 A | 2/1997 | Jacobs et al. | |
| 5,661,004 A | 8/1997 | Browning et al. | |
| 5,670,149 A | 9/1997 | Browning et al. | |
| 5,721,121 A | 2/1998 | Etcheverry et al. | |
| 5,726,039 A | 3/1998 | Oppenheim et al. | |
| 5,795,964 A | 8/1998 | Browning et al. | |
| 5,856,179 A | 1/1999 | Chen et al. | |
| 5,925,351 A | 7/1999 | Browning et al. | |
| 5,976,833 A | 11/1999 | Furukawa et al. | |
| 6,312,691 B1 | 11/2001 | Browning et al. | |
| 6,403,087 B1 | 6/2002 | Browning et al. | |
| 6,669,941 B1 | 12/2003 | Browning et al. | |
| 7,001,598 B2 | 2/2006 | Browning et al. | |
| 7,030,080 B2 | 4/2006 | Browning et al. | |
| 7,060,667 B1 | 6/2006 | Browning et al. | |
| 7,255,854 B1 | 8/2007 | Browning et al. | |
| 7,294,481 B1 | 11/2007 | Fung | |
| 7,309,492 B2 | 12/2007 | Browning et al. | |
| 7,427,403 B2 | 9/2008 | Browning et al. | |
| 7,452,530 B2 | 11/2008 | Browning et al. | |
| 7,459,537 B2 | 12/2008 | Browning et al. | |
| 2002/0001585 A1 | 1/2002 | Browning et al. | |
| 2002/0039580 A1 | 4/2002 | Browning et al. | |
| 2002/0197254 A1 | 12/2002 | Browning et al. | |
| 2004/0058394 A1 | 3/2004 | Garber et al. | |
| 2004/0198635 A1 | 10/2004 | Browning et al. | |
| 2005/0037003 A1 | 2/2005 | Browning et al. | |
| 2005/0281811 A1 | 12/2005 | Browning et al. | |
| 2006/0104971 A1 | 5/2006 | Garber et al. | |
| 2006/0134102 A1 | 6/2006 | LePage et al. | |
| 2006/0222644 A1 | 10/2006 | Garber et al. | |
| 2006/0280722 A1 | 12/2006 | Browning et al. | |
| 2007/0116668 A1 | 5/2007 | Browning et al. | |
| 2007/0154476 A1 | 7/2007 | Browning et al. | |
| 2008/0076155 A1 | 3/2008 | Fung | |
| 2008/0219967 A1 | 9/2008 | Browning et al. | |

FOREIGN PATENT DOCUMENTS

| | | |
|---|---|---|
| DE | 3218121 A1 | 11/1983 |
| EP | 0058481 B1 | 8/1982 |
| EP | 0367575 A1 | 5/1990 |
| EP | 0496973 B1 | 8/1992 |
| EP | 0509553 B1 | 10/1992 |
| EP | 0608532 A2 | 8/1994 |
| EP | 0873998 A2 | 10/1998 |
| WO | WO-91/00347 A1 | 1/1991 |
| WO | WO-92/00329 A1 | 1/1992 |
| WO | WO-94/04679 A1 | 3/1994 |
| WO | WO-94/06476 A1 | 3/1994 |
| WO | WO-94/13808 A2 | 6/1994 |
| WO | WO-96/01121 A1 | 1/1996 |
| WO | WO-96/22788 A1 | 8/1996 |
| WO | WO-96/23071 A2 | 8/1996 |
| WO | WO-97/03678 A1 | 2/1997 |
| WO | WO-97/03687 A1 | 2/1997 |
| WO | WO-97/04658 A1 | 2/1997 |
| WO | WO-97/41895 A2 | 11/1997 |
| WO | WO-98/17313 A2 | 4/1998 |

(Continued)

OTHER PUBLICATIONS

Gommerman JL, et al. J. Clin. Invest. 112(5):755-767, Sep. 1, 2003.*

(Continued)

*Primary Examiner* — Robert Landsman
(74) *Attorney, Agent, or Firm* — Nelson Mullins Riley & Scarborough LLP; Megan E. Williams

(57) ABSTRACT

Methods of treating a demyelinating disorder using inhibitors of the lymphotoxin pathway.

32 Claims, 6 Drawing Sheets

FOREIGN PATENT DOCUMENTS

| WO | WO-98/18928 A1 | 5/1998 |
| --- | --- | --- |
| WO | WO-98/25967 A1 | 6/1998 |
| WO | WO-99/53059 A1 | 10/1999 |
| WO | WO-2007/146414 A2 | 12/2007 |

OTHER PUBLICATIONS

Lin X et al., International Immunology 15(8):955-962, 2003.*
Plant SR, et al. Presentation No. 213.2, Neuroscience Meeting Planner, New Orleans, LA, Society for Neuroscience, 2003.*
Abe, Yasuhito et al., "Expression of Membraine-associated Lymphotoxin/Tumor Necrosis Factor-β on Human Lymphokine-activated Killer Cells," *Jpn. J. Cancer Res.*, vol. 82:23-26 (1991).
Abe, Yasuhito et al., "Studies of Membrane-Associated and Soluble (Secreted) Lymphotoxin in Human Lymphokine-Activated T-Killer Cells in Vitro," *Lymphokine and Cytokine Research*, vol. 11(2):115-121 (1992).
Acharya, S.K. et al., "A preliminary open trial on interferon stimulator (SNMC) derived from *Glycyrrhiza glabra* in the treatment of subacute hepatic failure," *Indian J. Med. Res. [B]*, vol. 98:69-74 (1993).
Aebersold, Ruedi H. et al., "Internal amino acid sequence analysis of proteins separated by one- or two-dimensional gel electrophoresis after in situ protease digestion on nitrocellulose," *Proc. Natl. Acad. Sci. USA*, vol. 84:6970-6974 (1987).
Aggarwal, Bharat B. et al., "Human Lymphotoxin," *The Journal of Biological Chemistry*, vol. 259(1):686-691 (1984).
Aggarwal, Bharat B. et al., "Primary Structure of Human Lymphotoxin Derived from 1788 Lymphoblastoid Cell Line," *The Journal of Biological Chemistry*, vol. 260(4):2334-2344 (1985).
Aggarwal, Bharat B. et al., "Tumor necrosis factors: Developments during the last decade," *Eur. Cytokine Netw.*, vol. 7(2):93-124 (1996).
Akashi, Makoto et al., "Lymphotoxin: Stimulation and Regulation of Colony-Stimulating Factors in Fibroblasts," *Blood*, vol. 74(7):2383-2390 (1989).
Alderson, Mark R. et al., "Molecular and biological characterization of human 4-1BB and its ligand," *Eur. J. Immunol.*, vol. 24:2219-2227 (1994).
Alderson, Mark R. et al., "Regulation of apoptosis and T cell activation by Fas-specific mAb," *International Immunology*, vol. 6(11):1799-1806 (1994).
Alexopoulou, Lena et al., "Immunoregulatory Activities of Transmembrane TNF Revealed in Transgenic and Mutant Mice," *6th international TNF Congress*, p. 228, No. 110 (1996).
Alimzhanov, Marat B. et al., "Abnormal development of secondary lymphoid tissues in lymphotoxin β-deficient mice," *Proc. Natl. Acad. Sci. USA*, vol. 94:9302-9307 (1997).
Amiri, Payman et al., "Tumour necrosis factor α restores granulomas and induces parasite egg-laying in schistosome-infected SCID mice," *Nature*, vol. 356:604-607 (1992).
Anderson, W. French, "Human gene therapy," *Nature*, vol. 392:25-30 (1998).
Andersson, Ulf et al., "Characterization of individual tumor necrosis factor α- and β-producing cells after polyclonal T cell activation," *Journal of Immunological Methods*, vol. 123:233-240 (1989).
Andrews, Janet S. et al., "Characterization of the Receptor for Tumor Necrosis Factor (TNF) and Lymphotoxin (LT) on Human T Lymphocytes, TNF and LT Differ in Their Receptor Binding Properties and the Induction of MHC Class I Proteins on a Human CD4+ T Cell Hybridoma," *The Journal of Immunology*, vol. 144(7):2582-2591 (1990).
Androlewicz, Matthew J. et al., "Lymphotoxin Is Expressed as a Hetermeric Complex with a Distinct 33-kDa Glycoprotein on the Surface of an Activated Human T Cell Hybridoma," *The Journal of Biological Chemistry*, vol. 267(4):2542-2547 (1992).
Armitage, Richard J. et al., "Molecular and biological characterization of a murine ligand for CD40," *Nature*, vol. 357:80-82 (1992).
Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," *J. Exp. Med.*, vol. 177:1439-1450 (1993).
Ashkenazi, Avi et al., "Protection against endotoxic shock by a tumor necrosis factor receptor immunoadhesin," *Proc. Natl. Acad. Sci. USA*, vol. 88:10535-10539 (1991).

Badenhoop, K. et al., "TNF-α gene polymorphisms in Type 1 (insulin-dependent) diabetes mellitus," *Diabetologia*, vol. 32:445-448 (1989).
Baens, Mathijs et al., "Construction and Evaluation of a hncDNA Library of Human 12p Transcribed Sequences Derived from a Somatic Cell Hybrid," *Genomics*, vol. 16:214-218 (1993).
Banks, Theresa A. et al., "Lymphotoxin-α-Deficient Mice," *The Journal of Immunology*, vol. 155:1685-1693 (1995).
Banner, David W. et al., "Crystal Structure of the Soluble Human 55 kd TNF Receptor-Human TNFβ Complex: Implications for TNF Receptor Activation," *Cell*, vol. 73:431-445 (1993).
Barnetson, "Hypersensitivity—Type IV," Mosby-Year Book Europe Ltd., Chpt. 22, pp. 22.1-22.12 (1993).
Baum, Peter R. et al., "Molecular characterization of murine and human OX40/OX40 ligand systems: identification of a human OX40 ligand as the HTLV0-1-regulated protein gp34," *The EMBO Journal*, vol. 13(17):3992-4001 (1994).
Bernstein, David I. et al., "Effects of therapy with an immunomodulator (imiquimod, R-837) alone with the acyclovir on genital HSV-2 infection in guinea-pigs when begun after lesion development," *Antiviral Research*, vol. 20:45-55 (1993).
Bethell, Delia B. et al., "Pathophysiologic and Prognostic Role of Cytokines in Dengue Hemorrhagic Fever," *JID*, vol. 177:778-782 (1998).
Beutler, B. et al., "Passive Immunization Against Cachectin/Tumor Necrosis Factor Protects Mice from Lethal Effect of Endotoxin," *Science*, vol. 229:869-871 (1985).
Beutler, Bruce et al., "The History, Properties, and Biological Effects of Cachectin," *Biochemistry*, vol. 27(20):7575-7582 (1988).
Bloemkolk, Jan-Willem et al., "Effect of Temperature on Hybridoma Cell Cycle and MAb Production," *Biotechnology and Bioengineering*, vol. 40:427-431 (1992).
Bork, Peer, "Powers and Pitfalls in Sequence Analysis: The 70% Hurdle," *Genome Research*, vol. 10:398-400 (2000).
Borth, Nicole et al., "Growth and production kinetics of human X mouse and mouse hybridoma cells at reduced temperature and serum content," *Journal of Biotechnology*, vol. 25:319-331 (1992).
Bowen, Michael A. et al., "Structure and Expression of Murine CD30 and Its Role in Cytokine Production," *The Journal of Immunology*, vol. 156:442-449 (1996).
Bowie, James U. et al., "Deciphering the Message in Protein Sequences: Tolerance to Amino Acid Substitutions," *Science*, vol. 247:1306-1310 (1990).
Bringman, Timothy S. et al., "Monoclonal Antibodies to Human Tumor Necrosis Factors Alpha and Beta: Application for Affinity Purification, Immunoassays, adn as Structural Probes," *Hybridoma*, vol. 6(5):489-507 (1987).
Briskin, Michael J. et al., "MAdCAM-1 has homology to immunoglobulin and mucin-like adhesion receptors and to IgA1," *Nature*, vol. 363:461-464 (1993).
Browning, Jeffrey L. et al., "Characterization of Surface Lymphotoxin Forms, Use of Specific Monoclonal Antibodies and Soluble Receptors," *The Journal of Immunology*, vol. 154:33-46 (1995).
Browning, Jeffrey L. et al., "Lymphotoxin and an Associated 33-kDa Glycoprotein Are Expressed on the Surface of an Activated Human T Cell Hybridoma," *The Journal of Immunology*, vol. 147(4):1230-1237 (1991).
Browning, Jeffrey L. et al., "Lymphotoxin β, a Novel Member of the TNF Family That Forms a Heteromeric Complex with Lymphotoxin on the Cell Surface," *Cell*, vol. 72:847-856 (1993).
Browning, Jeffrey L. et al., "Preparation and Characterization of Soluble Recombinant Heterotrimeric Complexes of Human Lymphotoxins α and β," *The Journal of Biological Chemistry*, vol. 271(15):8618-8626 (1996).
Browning, Jeffrey L. et al., "Signaling through the Lymphotoxin β Receptor Induces the Death of Some Adenocarcinoma Tumor Lines," *J. Exp. Med.*, vol. 183:867-878 (1996).
Browning, Jeffrey et al., "Studies on the Differing Effects of Tumor Necrosis Factor and Lymphotoxin on the Growth of Several Human Tumor Lines," *The Journal of Immunology*, vol. 143(6):1859-1867 (1989).

Bucay, Nathan et al., "Osteoprotegerin-deficient mice develop early onset osteoporosis and arterial calcification," *Genes & Development*, vol. 12:1260-1268 (1998).

Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111:2129-2138 (1990).

Cavender, Druie E. et al., "Endothelial Cell Activation Induced by Tumor Necrosis Factor and Lymphotoxin," *American Journal of Pathology*, vol. 134(3):551-560 (1989).

Cavender, Druie et al., "Pathways to chronic inflammation in rheumatoid synovitis," *Federation Proceedings*, vol. 46:113-117 (1987).

Cavert, Winston et al., "Kinetics of Response in Lymphoid Tissues to Antiretroviral Therapy of HIV-1 Infection," *Science*, vol. 276:960-964 (1997).

Chaplin, David D. et al., "Cytokine regulation of secondary lymphoid organ development," *Current Opinion in Immunology*, vol. 10:289-297 (1998).

Chen, Chyi-Ying A. et al., "AU-rich elements: characterization and importance in mRNA degradation," *TIBS*, vol. 20:465-470 (1995).

Cher, Daniel J. et al., "Two Types of Murine Helper T Cell Clone, II. Delayed-Type Hypersensitivity is Mediated by $T_H1$ Clones," *The Journal of Immunology*, vol. 138(11):3688-3694 (1987).

Chicheportiche, Yves et al., "TWEAK, a New Secreted Ligand in the Tumor Necrosis Factor Family That Weakly Induces Apoptosis," *The Journal of Biological Chemistry*, vol. 272(51):32401-32410 (1997).

Chisholm, Patricia L. et al., "Monoclonal antibodies to the integrin α-4 subunit inhibit the murine contact hypersensitivity response," *Eur. J. Immunol.*, vol. 23:682-688 (1993).

Chuppa, Sandra et al., "Fermentor Temperature as a Tool for Control of High-Density Perfusion Cultures of Mammalian Cells," *Biotechnol. Bioeng.*, vol. 55:328-338 (1997).

Corcoran, Anne E. et al., "Characterization of ligand binding by the human p55 tumour-necrosis-factor receptor, Involvement of individual cysteine-rich repeats," *Eur. J. Biochem.*, vol. 223:831-840 (1994).

Corcoran, A.E. et al., "Minimal tumor necrosis factor receptor binding protein: optimum biological activity of a truncated p55 soluble tumor necrosis factor receptor-IgG fusion protein," *European Cytokine Network*, vol. 9(3):255-262 (1998).

Cotran, Ramzi S. et al., "Endothelial Activation, Its Role in Inflammatory and Immune Reactions," *Endothelial Cell Biology in Health and Disease*, Chpt. 15, pp. 335-347 (1988).

Crowe, Paul D. et al., "A Lymphotoxin-β-Specific Receptor," *Science*, vol. 264:707-708 (1994).

Crowe, Paul D. et al., "Production of lymphotoxin (LTα) and a soluble dimeric form of its receptor using the baculovirus expression system," *Journal of Immunological Methods*, vol. 168:79-89 (1994).

Damle, Nitin K. et al., "Distinct Regulatory Effects of IL-4 and TNF-α During CD3-Dependent and CD3-Independent Initiation of Human T-Cell Activation," *Lymphokine Research*, vol. 8(2):85-97 (1989).

Degli-Esposti, Mariapia A. et al., "Activation of the Lymphotoxin β Receptor by Cross-Linking Induces Chemokine Production and Growth Arrest in A375 Melanoma Cells," *The Journal of Immunology*, vol. 158:1756-1762 (1997).

Dermer, Gerald B., "Another Anniversary for the War on Cancer," *BioTechnology*, vol. 12:320 (1994).

De Togni, Pietro et al., "Abnormal Development of Peripheral Lymphoid Organs in Mice Deficient in Lymphotoxin," *Science*, vol. 264:703-707 (1994).

Dhein, Jens et al., "Induction of Apoptosis by Monoclonal Antibody Anti-APO-1 Class Switch Variants is Dependent on Cross-linking of APO-1 Cell Surface Antigens," *The Journal of Immunology*, vol. 149(10):3166-3173 (1992).

Dighe, Anand S. et al., "Enhanced In Vivo Growth and Resistance to Rejection of Tumor Cells Expressing Dominant Negative IFNγ Receptors," *Immunity*, vol. 1:447-456 (1994).

Dijkstra, Christine D. et al., "Marginal zone macrophages identified by a monoclonal antibody: characterization of immuno- and enzyme-histochemical properties and functional capacities," *Immunology*, vol. 55:23-30 (1985).

Doumbou, Cyr Lézin et al., "Selection and Characterization of Microorganisms Utilizing THaxtomin A, a Phytotoxin Produced by *Streptomyces scabies*," *Applied and Environmental Microbiology*, vol. 64(11):4313-4316 (1998).

Düzgünes, Nejat et al., "Liposome Targeting to HIV-Infected Cells Via Recombinant Soluble CD4 and CD4-IgG (Immunoadhesin)," *Journal of Cellular Biochemistry*, vol. 16:77, No. Q514 (1992).

Eason, James D. et al., "Evaluation of Recombinant Human Soluble Dimeric Tumor Necrosis Factor Receptor for Prevention of OKT3-Associated Acute Clinical Syndrome," *Transplantation*, vol. 61(2):224-228 (1996).

Eck, Michael J. et al., "The Structure of Tumor Necrosis Factor-α at 2.6 Å Resolution, Implications for Receptor Binding," *The Journal of Biological Chemistry*, vol. 264(29):17595-17605 (1989).

Eck, Michael J. et al., "The Structure of Human Lymphotoxin (Tumor Necrosis Factor-β) at 1.9-Å Resolution," *The Journal of Biological Chemistry*, vol. 267(4):2119-2122 (1992).

Eggermont, Alexander M.M. et al., "Isolated Limb Perfusion With High-Dose Tumor Necrosis Factor-α in Combination With Interferon-γ and Melphalan for Nonresectable Extremity Soft Tissue Sarcomas: A Multicenter Trial," *Journal of Clinical Oncology*, vol. 14(10):2653-2665 (1996).

Endres, Robert et al., "Mature Follicular Dendritic Cell Networks Depend on Expression of Lymphotoxin β Receptor by Radioresistant Stromal Cells and of Lymphotoxin β and Tumor Necrosis Factor by B Cells," *J. Exp. Med.*, vol. 189(1):159-167 (1999).

Eppstein, Deborah A. et al., "Biological activity of liposome-encapsulated murine interferon γ is mediated by a cell membrane receptor," *Proc. Natl. Acad. Sci. USA*, vol. 82:3688-3692 (1985).

Erickson, Sharon L. et al., "Decreased sensitivity to tumour-necrosis factor but normal T-cell development in TNF receptor-2-deficient mice," *Nature*, vol. 372:560-563 (1994).

Ettinger, Rachel et al., "Disrupted splenic architecture, but normal lymph node development in mice expressing a soluble lymphotoxin-β receptor-IgG1 fusion protein," *Proc. Natl. Acad. Sci. USA*, vol. 93:13102-13107 (1996).

Fägerstam, Lars G. et al., "Surface Plasmon Resonance Detection in Affinity Technologies," *Handbook of Affinity Chromatography*, Chpt. 9, pp. 229-252 (1993).

Fanslow, William C. et al., "Soluble Forms of CD40 Inhibit Biologic Responses of Human B Cells," *The Journal of Immunology*, vol. 149(2):655-660 (1992).

Farrah, Terry et al., "Emerging cytokine family," *Nature*, vol. 358:26 (1992).

Feldmann, Marc et al., "Anti-Tumor Necrosis Factor-α Therapy of Rheumatoid Arthritis," *Advances in Immunology*, vol. 64:283-350 (1997).

Fitch, F.W. et al., "Differential Regulation of Murine T Lymphocyte Subsets," *Annu. Rev. Immunol.*, vol. 11:29-48 (1993).

Flier, Jeffrey S. et al., "The Tumor Necrosis Factor Ligand and Receptor Families," *Seminars in Medicine of the Beth Israel Hospital*, Boston, vol. 334(26):1717-1725 (1996).

Force, Walker R. et al., "Mouse Lymphotoxin-β Receptor," *The Journal of Immunology*, vol. 155:5280-5288 (1995).

Forster, Simon J. et al., "Expression of Foreign Genes in Mammalian Cells Using an Antibody Fusion System," *Molecular Biotechnology*, vol. 1:251-263 (1994).

Foy, Teresa M. et al., "gp39-CD40 Interactions Are Essential for Germinal Center Formation and the Development of B Cell Memory," *J. Exp. Med.*, vol. 180:157-163 (1994).

Freshney, R. Ian et al., Culture of Animal Cells, A Manual of Basic Technique, Second Edition, Alan R. Liss, Inc., New York, Chpt. 1, p. 4 (1987).

Fu, Yang-Xin et al., "B Lymphocytes Induce the Formation of Follicular Dendritic Cell Clusters in a Lymphotoxin α-dependent Fashion," *J. Exp. Med.*, vol. 187(7):1009-1018 (1998).

Fu, Yang-Xin et al., "Development and Maturation of Secondary Lymphoid Tissues," *Annu. Rev. Immunol.*, vol. 17:399-433 (1999).

Fu, Yang-Xin et al., "Lymphotoxin-α (LTα) Supports Development of Splenic Follicular Structure That Is Required for IgG Responses," *J. Exp. Med.*, vol. 185(12):2111-2120 (1997).

Fuh, Germaine et al., "Rational Design of Potent Antagonists to the Human Growth Hormone Receptor," *Science*, vol. 256:1677-1680 (1992).

Fukushima, Keiko et al., "N-Linked Sugar Chain Structure of Recombinant Human Lymphotoxin Produced by CHO Cells: The Functional Role of Carbohydrate as to Its Lectin-like Character and Clearance Velocity," *Archives of Biochemistry and Biophysics*, vol. 304(1):144-153 (1993).

Furukawa, Kazuaki et al., "Effect of culture temperature on a recombinant CHO cell line producing a C-terminal α-amidating enzyme," *Cytotechnology*, vol. 26:153-164 (1998).

Fütterer, Agnes et al., "The Lymphotoxin β Receptor Controls Organogenesis and Affinity Maturation in Peripheral Lymphoid Tissues," *Immunity*, vol. 9:59-70 (1998).

Gatanaga, Tetsuya et al., "Purification and characterization of an inhibitor (soluble tumor necrosis factor receptor) for tumor necrosis factor and lymphotoxin obtained from the serum ultrafiltrates of human cancer patients," *Proc. Natl. Acad. Sci. USA*, vol. 87:8781-8784 (1990).

Giard, Donald J. et al., "Effect of Temperature on the Production of Human Fibroblast Interferon (41411)," *Proceedings of the Society for Experimental Biology and Medicine*, vol. 170:155-159 (1982).

Goeddel, D.V. et al., "Tumor Necrosis Factors: Gene Structure and Biological Activities," *Cold Spring Harbor Symposia Quantitative Biology*, vol. LI:597-609 (1986).

Gommerman, Jennifer L. et al., "Lymphotoxin/Light, Lymphoid Microenvironments and Autoimmune Disease," *Nat. Rev. Immunol.*, vol. 3(8):642-655 (2003).

Gonzalez, Mercedes et al., "The Sequential Role of Lymphotoxin and B Cells in the Development of Splenic Follicles," *J. Exp. Med.*, vol. 187(7):997-1007 (1998).

Goodwin, Raymond G. et al., "Molecular and Biological Characterization of a Ligand for CD27 Defines a New Family of Cytokines with Homology to Tumor Necrosis Factor," *Cell*, vol. 73:447-456 (1993).

Granger, Gale A. et al., "Lymphocyte in Vitro Cytotoxicity: Mechanisms of Immune and Non-Immune Small Lymphocyte Mediated Target L Cell Destruction," *The Journal of Immunology*, vol. 101(1):111-120 (1968).

Gray, Patrick W. et al., "Cloning and expression of cDNA for human lymphotoxin, a lymphokine with tumour necrosis activity," *Nature*, vol. 312:721-724 (1984).

Gray, Patrick W., "Molecular Characterization of Human Lymphotoxin," *Lymphokines*, vol. 13:199-208 (1987).

Green, Douglas R. et al., "Fas-ligand: Privilege and peril," *Proc. Natl. Acad. Sci. USA*, vol. 94:5986-5990 (1997).

Green, Lora M. et al., "Cytotoxic Lymphokines Produced by Cloned Human Cytotoxic T Lymphocytes, I. Cytotoxins Produced by Antigen-Specific and Natural Killer-Like CTL Are Dissimilar to Classical Lymphotoxins," *The Journal of Immunology*, vol. 135(6):4034-4043 (1985).

Green, Lora M. et al., "Rapid Colormetric Assay for Cell Viability: Application to the Quantitation of Cytotoxic and Growth Inhibitory Lymphokines," *Journal of Immunological Methods*, vol. 70:257-268 (1984).

Gupta, Manisha et al., "CD8-Mediated Protection against Evola Virus Infection Is Perforin Dependent," *The Journal of Immunology*, vol. 174:4198-4202 (2005).

Györfy, Z. et al., "Alteration of the TNF Sensitivity and Membrane Viscosity of Target Cells," *Eur. Cytokine Netw.*, vol. 7(2):167 (1996).

Hagemeijer, A., "Cytogenics and oncogenes," *Leukemia*, vol. 6(Suppl. 4):16-18 (1992).

Han, Shuhua et al., "Cellular Interaction in Germinal Centers, Roles of CD40 Ligand and B7-2 in Established Germinal Centers," *The Journal of Immunology*, vol. 155:556-567 (1995).

Harris, William J. et al., "Therapeutic antibodies—the coming of age," *TibTech*, vol. 11:42-44 (1993).

Harrop, Jeremy A. et al., "Herpesvirus Entry Mediator Ligand (HVEM-L), a Novel Ligand for HVEM/TR2, Stimulates Proliferation of T Cells and Inhibits HT29 Cell Growth," *The Journal of Biological Chemistry*, vol. 273(42):27548-27556 (1998).

Havell, Edward A. et al., "The Antitumor Function of Tumor Necrosis Factor (TNF) I. Therapeutic Action of TNF against an Established Murine Sarcoma is Indirect, Immunologically Dependent, and Limited by Severe Toxicity," *J. Exp. Med.*, vol. 167:1067-1085 (1988).

Heath, Sonya L. et al., "Follicular dendritic cells and human immunodeficiency virus infectivity," *Nature*, vol. 377:740-744 (1995).

Higuchi, Masahiro et al., "Inhibition of Ligand Binding and Antiproliferative Effects of Tumor Necrosis Factor and Lymphotoxin by Soluble Forms of Recombinant P60 and P80 Receptors," *Biochemical and Biophysical Research Communications*, vol. 182(2):638-643 (1992).

Hipp, Jason D. et al., "Cancer Vaccines: An Update," *In Vivo*, vol. 14:571-585 (2000).

Hiserodt, John C. et al., "Identification of Membrane-Associated Lymphotoxin (LT) on Mitogen-Activated Human Lymphocytes Using Heterologous Anti-LT Antisera in Vitro," *Cellular Immunology*, vol. 34:326-339 (1977).

Hober, Didier et al., "Serum Levels of Tumor Necrosis Factor-α (TNF-α), Interleukin-6 (IL-6), and Interleukin-1β (IL-1β) in Dengue-Infected Patients," *Am. J. Trop. Med. Hyg.*, vol. 48(3):324-331 (1993).

Huang, Sui et al., "Immune Response in Mice That Lack the Interferon-γ Receptor," *Science*, vol. 259:1742-1745 (1993).

Hudde, T. et al., "Activated polyamidoamine dendrimers, a non-viral vector for gene trasfer to the corneal endothelium," *Gene Therapy*, vol. 6:939-943 (1999).

Hwang, Karl J. et al., "Hepatic uptake and degradation of unilamellar sphingomyelin/cholesterol liposomes: A kinetic study," *Proc. Natl. Acad. Sci. USA*, vol. 77(7):4030-4034 (1980).

Invitrogen life technologies, "BaculoDirect™ Baculovirus Expression Systems," Instruction Manual, Version F (2004).

Itoh, Naoto et al., "The Polypeptide Encoded by the cDNA for Human Cell Surface Antigen Fas Can Mediate Apoptosis," *Cell*, vol. 66:233-243 (1991).

Jain, Rakesh K., "Vascular and interstitial barriers to delivery of therapeutic agents in tumors," *Cancer and Metastasis Reviews*, vol. 9:753-766 (1990).

Jalkanen, S. et al., "A Distinct Endothelial Cell Recognition System That Controls Lymphocyte Traffic into Inflamed Synovium," *Science*, vol. 233:556-558 (1986).

Jenkins, Nitel et al., "Temperature Control of Growth and Productivity in Mutant Chinese Hamster Ovary Cells Synthesizing a Recombinant Protein," *Biotechnology and Bioengineering*, vol. 42:1029-1036 (1993).

Johne, Berit et al., "Epitope mapping and binding kinetics of monoclonal antibodies studied by real time biospecific interaction analysis using surface plasmon resonance," *Journal of Immunological Methods*, vol. 160:191-198 (1993).

Jones, E.Y. et al., "Structure of tumour necrosis factor," *Nature*, vol. 338:225-228 (1989).

Juráková, Vera et al., "Interferon inducer, polyriboguanylic—polyribocytidylic acid, inhibits experimental hepatic metastases in mice," *European Journal of Pharmacology*, vol. 221:107-111 (1992).

Kasid, Attan et al., "Human gene transfer: Characterization of human tumor-infiltrating lymphocytes as vehicles for retroviral-mediated gene trasfer in man," *Proc. Natl. Acad. Sci. USA*, vol. 87:473-477 (1990).

Katz, Irene R. eta I., "Growth of SJL/J-Derived Transplantable Reticulum Cell Sarcoma as Related to Its Ability to Induce T-Cell Proliferation in the Host. III. Studies on Thymectomized and Congenitally Athymic SJL Mice," *Cellular Immunology*, vol. 65:84-92 (1981).

Katz, Jonathan D. et al., "T Helper Cell Subsets in Insulin-Dependent Diabetes," *Science*, vol. 268:1185-1188 (1995).

Kaufmann, Hitto et al., "Influence of Low Temperature on Productivity, Proteome and Protein Phosphorylation of CHO Cells," *Biotechnol. Bioeng.*, vol. 63:573-582 (1999).

Kawabe, Tsutomu et al., "The Immune Responses in CD40-Deficient Mice: Impaired Immunoglobulin Class Switching and Germinal Center Formation," *Immunity*, vol. 1:167-178 (1994).

Kinkhabwala, M. et al., "A Novel Addition to the T Cell Repertory Cell Surface Expression of Tumor Necrosis Factor/Cachectin by Activated Normal Human T Cells," *J. Exp. Med.*, vol. 171:941-946 (1990).

Kohno, Tadahiko et al., "A second tumor necrosis factor receptor gene product can shed a naturally occurring tumor necrosis factor inhibitor," *Proc. Natl. Acad. Sci. USA*, vol. 87:8331-8335 (1990).

Kolanus, Waldemar et al., "T Cell Activation by Clustered Tyrosine Kinases," *Cell*, vol. 74:171-183 (1993).

Kopp, William C. et al., "Immunomodulatory Effects of Interferon-γ in Patients with Metastatic Malignant Melanoma," *J. Immunother.*, vol. 13(3):181-190 (1993).

Kraal, Georg, "Cells in the Marginal Zone of the Spleen," *International Review of Cytology*, vol. 132:31-74 (1992).

Kraal, Georg et al., "Expression of the Mucosal Vascular Addressin, MAdCAM-1, on Sinus-Lining Cells in the Spleen," *American Journal of Pathology*, vol. 147(3):763-771 (1995).

Kraal, G. et al., "Lymphocyte migration in the spleen: the effect of macrophage elimination," *Immunology*, vol. 68:227-232 (1989).

Kraal, G. et al., "Marginal metallophilic cells of the mouse spleen identified by a monoclonal antibody," *Immunology*, vol. 58:665-669 (1986).

Kratz, Alexander et al., "Chronic Inflammation Caused by Lymphotoxin Is Lymphoid Neogenesis," *J. Exp. Med.*, vol. 183:1461-1472 (1996).

Kriegler, M. et al., "A Novel Form of TNF/Cachectin Is a Cell Surface Cytotoxic Transmembrane Protein: Ramifications for the Complex Physiology of TNF," *Cell*, vol. 53:45-53 (1988).

Kwon, Byoung S. et al., "A Newly Identified Member of the Tumor Necrosis Factor Receptor Superfamily with a Wide Tissue Distribution and Involvement in Lymphocyte Activation," *The Journal of Biological Chemistry*, vol. 272(22):14272-14276 (1997).

Lacy, Mark D. et al., "Viral Hemorrhagic Fevers," *Advances in Pediatric Infectious Diseases*, vol. 12:21-53 (1997).

Laman, Jon D. et al., "Functions of CD40 and Its Ligand, gp39 (CD40L)," *Critical Reviews in Immunology*, vol. 16:59-108 (1996).

Lane, Peter et al., "Activated human T cells express a ligand for the human B cell-associated antigen CD40 which participates in T cell-dependent activation of B lymphocytes," *Eur. J. Immunol.*, vol. 22:2573-2578 (1992).

Langer, Robert et al., "Biocompatibility of polymeric delivery systems for macromolecules," *Journal of Biomedical Materials Research*, vol. 15:267-277 (1981).

Langer, Robert, "Controlled release of macromolecules," *Chemtech*, pp. 98-105 (1982).

Lasky, J.L. et al., "Characterization and Growth Factor Requirements of SJL Lymphoma, I. Development of a B Cell Growth Factor-Dependent in Vitro Cell Line, cRCS-X," *The Journal of Immunology*, vol. 14:679-687 (1988).

Lasky, Jennifer L. et al., "Characterization and growth factor requirements of SJL lymphomas II. Interleukin 5 dependence on the in vitro cell line, cRCS-X, and influence of other cytokines," *Eur. J. Immunol.*, vol. 19:365-371 (1989).

Lawton, Pornsri et al., "Characterization of the Mouse Lymphotoxin-β Gene," *The Journal of Immunology*, vol. 154:239-246 (1995).

Lazar, Eliane et al., "Transforming Growth Factor α: Mutation of Aspartic Acid 47 and Leucine 48 Results in Different Biological Activities," *Molecular and Cellular Biology*, vol. 8(3):1247-1252 (1988).

Le Hir, Michel et al., "Differentiation of Follicular Dendritic Cells and Full Antibody Responses Require Tumor Necrosis Factor Receptor-1 Signaling," *J. Exp. Med.*, vol. 183:2367-2372 (1996).

Lee, Won-Ha et al., "Tumor Necrosis Factor Receptor Superfamily 14 is Involved in Atherogenesis by Inducing Proinflammatory Cytokines and Matrix Metalloproteinases," *Arterioscler. Thromb. Vasc. Biol.*, vol. 21:2004-2010 (2001).

Luettig, Birgit et al., "Evidence for the Existence of Two Forms of Membrane Tumor Necrosis Factor: An Integral Protein and a Molecule Attached to its Receptor," *The Journal of Immunology*, vol. 143(12):4034-4038 (1989).

Liang, Chi-Ming et al., "Production and Characterization of Monoclonal Antibodies Against Recombinant Human Tumor Necrosis Factor/Cachectin," *Biochemical and Biophysical Research Communications*, vol. 137(2):847-854 (1986).

Ling, Leona E. et al., "Human Type I Interferon Receptor, IFNAR, is a Heavily Glycosylated 120-130 kD Membrane Protein," *Journal of Interferon and Cytokine Research*, vol. 15:55-61 (1995).

Liu, Chau-Ching et al., "Identification and characterization of a membrane-bound cytotoxin of murine cytolytic lymphocytes that is related to tumor necrosis factor/cachectin," *Proc. Natl. Acad. Sci. USA*, vol. 86:3286-3290 (1989).

Liu, Chau-Ching et al., "Identification, Isolation, and Characterization of a Novel Cytotoxin in Murine Cytolytic Lymphocytes," *Cell*, vol. 51:393-403 (1987).

Loetscher, Hansruedi et al., "Recombinant 55-kDa Tumor Necrosis Factor (TNF) Receptor," *The Journal of Biological Chemistry*, vol. 266(27):18324-18329 (1991).

Ludwig, Andreas et al., "Influence of the temperature on the shear stress sensitivity of adherent BHK 21 cells," *Appl. Microbiol. Biotechnol.*, vol. 38:323-327 (1992).

Mackay, Fabienne et al., "Both the Lymphotoxin and Tumor Necrosis Factor Pathways Are Involved in Experimental Murine Models of Colitis," *Gastroenterology*, vol. 115:1464-1475 (1998).

Mackay, Fabienne et al., "Cytotoxic Activities of Recombinant Soluble Murine Lymphotoxin-α and Lymphotoxin-αβ Complexes," *The Journal of Immunology*, vol. 159:3299-3310 (1997).

Mackay, Fabienne et al., "Lymphotoxin but not tumor necrosis factor functions to maintain splenic architecture and humoral responsiveness in adult mice," *Eur. J. Immunol.*, vol. 27:2033-2042 (1997).

Mackay, Fabienne et al., "Turning off follicular dendritic cells," *Nature*, vol. 395:26-27 (1998).

MacLennan, I.C.M. et al., "The Structure and Function of Secondary Lymphoid Tissues," *Clinical Aspects of Immunology*, Blackwell Scientific Publications, 5th Edition, vol. 1, Chpt. 2, pp. 13-30 (1993).

Maeda, Kunihiko et al., "Murine Follicular Dendritic Cells and Low Affinity Fc Receptors for IgE (FcεRll)," *The Journal of Immunology*, vol. 148(8):2340-2347 (1992).

Mallett, Susan et al., "A new superfamily of cell surface proteins related to the nerve growth factor receptor," *Immunology Today*, vol. 12(7):220-223 (1991).

Marsters, Scot A. et al., "Identification of Cysteine-rich Domains of the Type 1 Tumor Necrosis Factor Receptor Involved in Ligand Binding," *The Journal of Biological Chemistry*, vol. 267(9):5747-5750 (1992).

Matsumoto, Mitsuru et al., "Affinity maturation without germinal centres in lymphotoxin-α-deficient mice," *Nature*, vol. 382:462-466 (1996).

Matsumoto, Mitsuru et al., "Distinct Roles of Lymphotoxin α and the Type 1 Tumor Necrosis Factor (TNF) Receptor in the Establishment of Follicular Dendritic Cells from the Non-Bone Marrow-derived Cells," *J. Exp. Med.*, vol. 186(12):1997-2004 (1997).

Matsumoto, Mitsuru et al., "Lymphotoxin-α-deficient and TNF receptor-I-deficient mice define developmental and functional characteristics of germinal centers," *Immunological Reviews*, vol. 156:137-144 (1997).

Matsumoto, Mitsuru et al., "Role of Lymphotoxin and the Type I TNF Receptor in the Formation of Germinal Centers," *Science*, vol. 271:1289-1291 (1996).

Mauri, Davide N. et al., "Light, a New Member of the TNF Superfamily, and Lymphotoxin α Are Ligands for Herpesvirus Entry Mediator," *Immunity*, vol. 8:21-30 (1998).

Mendlovic, Shlomo et al., "Induction of a systemic lupus erythematosus-like disease in mice by a common human anti-DNA idiotype," *Proc. Natl. Acad. Sci. USA*, vol. 85:2260-2264 (1988).

Merriam-Webster Online Dictionary, "composition," (2004).

Miller, Glenn T. et al., "Specific Interaction of Lymphocyte Function-associated Antigen 3 with CD2 Can Inhibit T Cell Responses," *J. Exp. Med.*, vol. 178:211-222 (1993).

Modlin, Robert L. et al., "Type 2 cytokines and negative immune regulation in human infections," *Current Opinion in Immunology*, vol. 5:511-517 (1993).

Mohan, Chandra et al., "Interaction Between CD40 and Its Ligand gp39 in the Development of Murine Lupus Nephritis," *The Journal of Immunology*, vol. 154:1470-1480 (1995).

Mohler, Kendall M. et al., "Suluble Tumor Necrosis Factor (TNF) Receptors Are Effective Therapeutic Agents in Lethal Endotoxemia and Function Simultaneously as Both TNF Carriers and TNF Antagonists," *Journal of Immunology*, vol. 151:1548-1561 (1993).
Montgomery, Rebecca I. et al., "Herpes Simplex Virus-1 Entry into Cells Mediated by a Novel Member of the TNF/NGF Receptor Family," *Cell*, vol. 87:427-436 (1996).
Morrison, Sherie L. et al., "Chimeric human antibody molecules: Mouse antigen-binding domains with human constant region domains," *Proc. Natl. Acad. Sci. USA*, vol. 81:6851-6855 (1984).
Morrison, Sherie L., "In Vitro Antibodies: Strategies for Production and Application," *Annu. Rev. Immunol.*, vol. 10:239-265 (1992).
Morrissey, Philip J. et al., "CD4+ T Cells That Expess High Levels of CD45RB Induce Wasting Disease When Transferred into Congenic Severe Combined Immunodeficient Mice. Disease Development is Prevented by Cotrasfer of Purified CD4+ T Cells," *J. Exp. Med.*, vol. 178:237-244 (1993).
Naismith, James H. et al., "Seeing Double: Crystal Structures of the Type I TNF Receptor," *Journal of Molecular Recognition*, vol. 9:113-117 (1996).
Nakache, Maurice et al., "The mucosal vascular addressin is a tissue-specific endothelial cell adhesion molecule for circulating lymphocytes," *Nature*, vol. 337:179-181 (1989).
Neumann, Brigitte et al., "Defective Peyer's Patch Organogenesis in Mice Lacking the 55-kD Receptor for Tumor Necrosis Factor," *J. Exp. Med.*, vol. 184:259-264 (1996).
Ngo, J. Thomas et al., "Computational Complexity, Protein Structure Prediction, and the Levinthal Paradox," *The Protein Folding Problem and Tertiary Structure Prediction*, Birkhauer, Kenneth M. Merz, Jr. (Ed.), Chpt. 14, pp. 433-506 (1994).
Nicola, Anthony V. et al., "Monoclonal Antibodies to Distinct Sites on Herpes Simplex Virus (HSV) Glycoprotein D Block HSV Binding to HVEM," *Journal of Virology*, vol. 72(5):3595-3601 (1998).
Niederle, Norbert et al., "Long-Term Treatment of Chronic Myelogenous Leukemia with Different Interferons: Results from Three Studies," *Leukemia and Lymphoma*, vol. 9:111-119 (1993).
Nilsson, Joakim et al., "Affinity Fusion Strategies for Detection, Purification, and Immobilization of Recombinant Proteins," *Protein Expression and Purification*, vol. 11:1-16 (1997).
Old, Lloyd J., "Tumor Necrosis Factor (TNF)," *Science*, vol. 230:630-632 (1985).
Onishi, Tetsuro et al., "A Study on Direct Antitumor Activity of Bropirimine (Oral Interferon Inducer) for Renal Cell Carcinoma," *Acta Urol. Jpn.*, vol. 40:195-200 (1994).
Pasparakis, Manolis et al., "Immune and Inflammatory Responses to TNFα Deficient Mice: A Critical Requirement for TNFα in Germinal Centre Formation and in the Maturation of the Humoral Immune Response," *Eur. Cytokine Network*, vol. 7(2):239, No. 132 (1996).
Pass, Harvey I. et al., "The Macrophage, TNF, and Other Cytokines," *Basic Biology for the Thoracic Surgeon*, vol. 5(1):73-90 (1995).
Paul, Nina L. et al., "Lymphotoxin Activation by Human T-Cell Leukemia Virus Type I-Infected Cell Lines: Role of NF-κB," *Journal of Virology*, vol. 64(11):5412-5419 (1990).
Paul, Nina L. et al., "Lymphotoxin," *Ann. Rev. Immunol.*, vol. 6:407-438 (1988).
Pennica, Diane et al., "Human tumour necrosis factor: precursor structure, expression and homology to lymphotoxin," *Nature*, vol. 312:724-729 (1984).
Peppel, Karsten et al., "A Tumor Necrosis Factor (TNF) Receptor-IgG Heavy Chain Chimeric Protein as a Bivalent Antagonist of TNF Activity," *J. Exp. Med.*, vol. 171:1483-1489 (1991).
Peterson, Andrew et al., "Monoclonal antibody and ligand binding sites of the T cell erythrocyte receptor (CD2)," *Nature*, vol. 329:842-846 (1987).
Pfeffer, Klaus et al., "Mice Deficient for the 55 kd Tumor Necrosis Factor Receptor Are Resistant to Endotoxic Shock, yet Succumb to L. monocytogenes Infection," *Cell*, vol. 73:457-467 (1993).
Picarella, Dominic E. et al., "Insulitis in transgenic mice expressing tumor necrosis factor β (lymphotoxin) in the pancreas," *Proc. Natl. Acad. Sci. USA*, vol. 89:10036-10040 (1992).
Picker, Louis J. et al., "Physiological and Molecular Mechanisms of Lymphocyte Homing," *Annu. Rev. Immunol.*, vol. 10:561-591 (1992).
Plant, Sheila R. et al., "Astroglial-Derived Lymphotoxin-α Exacerbates Inflammation and Demyelination, But Not Remyelination," *Glia*, vol. 49:1-14 (2004).
Plant, Sheila R. et al., "Lymphotoxin β Receptor (Lt(βR): Dual Roles in Demyelination and Remyelination and Successful Therapeutic Intervention Using LtβR-Ig Protein," *The Journal of Neuroscience*, vol. 27(28):7429-7437 (2007).
Pleskov, V.M. et al., "The receptor-mediated endocytosis of influenza viruses and low-density lipoproteins by tissue cells," *Vopr. Virusol.*, vol. 39(3):121-125 (1994).
Pociot, F. et al., "A Tumour Necrosis Factor Beta Gene Polymorphism in Relation to Monokine Secretion and Insulin-Dependent Diabetes Mellitus," *Scand. J. Immunol.*, vol. 33:37-49 (1991).
Ponzio, Nicholas M. et al., "Host-Tumor Interactions in the SJL Lymphoma Model," *Intern. Rev. Immunol.*, vol. 1:273-301 (1986).
Powell, Kenneth L. et al., "The antiviral effects of nitric oxide," *Trends in Microbiology*, vol. 3(3):81-88 (1995).
Powrie, Fiona et al., "Inhibition of Th1 Responses Prevents Inflammatory Bowel Disease in *scid* Mice Reconstituted with CD45RB$^{hi}$ CD4+ T Cells," *Immunity*, vol. 1:553-562 (1994).
Powrie, Fiona et al., "Phenotypically distinct subsets of CD4+ T cells induce or protect from chronic intestinal inflammation in C. B-17 *scid* mice," *International Immunology*, vol. 5(11):1461-1471 (1993).
Qin, Zhihai et al., "Human Lymphotoxin Has at Least Equal Antitumor Activity in Comparison to Human Tumor Necrosis Factor But Is Less Toxic in Mice," *Blood*, vol. 85(10):2779-2785 (1995).
Queen, Cary et al., "A humanized antibody that binds to the interleukin 2 receptor," *Proc. Natl. Acad. Sci. USA*, vol. 86:10029-10033 (1989).
Raitano, Arthur B. et al., "Tumor Necrosis Factor Up-regulates γ-Interferon Binding in a Human Carcinoma Cell Line," *The Journal of Biological Chemistry*, vol. 265(16):10466-10472 (1990).
Ranges, Gerald E. et al., "Tumor Necrosis Factor-α AS a Proliferative Signal for an IL-2-Dependent T Cell Line: Strict Species Specificity of Action," *The Journal of Immunology*, vol. 142:1203-1208 (1989).
Ranges, Gerald E. et al., "Tumor Necrosis Factor α/Cachectin is a Growth Factor for Thymocytes, Synergistic Interactions with Other Cytokines," *J. Exp. Med.*, vol. 167:1472-1478 (1988).
Reed, Steven G. et al., "T-cell and cytokine responses in leishmaniasis," *Current Opinion in Immunology*, vol. 5:524-531 (1993).
Reisfeld, Ralph A. et al., "Involvement of B Lymphocytes in the Growth Inhibition of Human Pulmonary Melanoma Metastases in Athymic *nu/nu* Mice by an Antibody-Lymphotoxin Fusion Protein," *Cancer Research*, vol. 56:1707-1712 (1996).
Rennert, P.D. et al., "Normal Development of Lymph Nodes is Disrupted by Soluble LT beta Receptor—Ig Fusion Protein," *European Cytokine Network*, vol. 7(2):167, No. 17 (1996).
Rennert, Paul D. et al., "Selective disruption of lymphotoxin ligands reveals a novel set of mucosal lymph nodes and unique effects on lymph node cellular organization," *International Immunology*, vol. 9(11):1627-1639 (1997).
Rennert, Paul D. et al., "Surface Lymphotoxin α/β Complex Is Required for the Development of Peripheral Lymphoid Organs," *J. Exp. Med.*, vol. 184:1999-2006 (1996).
Renshaw, Blair R. et al., "Humoral Immune Response in CD40 Ligand-deficient Mice," *J. Exp. Med.*, vol. 180:1889-1900 (1994).
Reutershealth, "Systemic Lupus Erythematosus," retrieved online at http://www.reutershealth.com/wellconnected/doc63.html (2002).
Reuveny, S. et al., "Effect of temperature and oxygen on cell growth and recombinant protein production in insect cell cultures," *Appl. Microbiol. Biotechnol.*, vol. 38:619-623 (1993).
Roitt, Ivan M. et al., "Antibody Effector Functions," *Immunology*, Third Edition, Mosby, p. 4.8 (1993).
Roitt, Ivan M. et al., "Introduction to the Immune System," *Immunology*, Third Edition, Mosby, Chpt. 1, pp. 1.1-1.12 (1993).
Roitt, Ivan M. et al., "Hypersensitivity—Type I," *Immunology*, Third Edition, Mosby, Chpt. 19, pp. 19.1-19.22 (1993).
Romagnani, Sergio, "Lymphokine Production by Human T Cells in Disease States," *Annu. Rev. Immunol.*, vol. 12:227-257 (1994).
Roodman, G. David et al., "Tumor Necrosis Factor-alpha and Hematopoietic Progenitors: Effects of Tumor Necrosis Factor on the Growth of Erythroid Progenitors CFU-E and BFU-E and the Hematopoietic Cell Lines K562, HL60, and HEL Cells," *Exp. Hematol.*, vol. 15:928-935 (1987).
Rosenberg, Steven A. et al., "Use of Tumor-infiltrating Lymphocytes and Interleukin-2 in the Immunotherapy of Patients with Metastatic Melanoma," *The New England Journal of Medicine*, vol. 319(25):1676-1680 (1988).
Rothe, Joachim et al., "Mice lacking the tumour necrosis factor receptor 1 are resistant to TNF-mediated toxicity but highly susceptible to infection by *Listeria monocytogenes*," *Nature*, vol. 364:798-802 (1993).
Ruddle, Nancy H. et al., "An Antibody to Lymphotoxin and Tumor Necrosis Factor Prevents Transfer of Experimetnal Allergic Encephalomyelitis," *J. Exp. Med.*, vol. 172:1193-1200 (1990).
Ruddle, Nancy H. et al., "Cytotoxicity Mediated by Soluble Antigen and Lymphocytes in Delayed Hypersensitivity, III. Analysis of Mechanism," *The Journal of Experimental Medicine*, vol. 128:1267-1279 (1968).
Ruddle, Nancy H., "Lymphotoxin redux," *Immunology Today*, vol. 6(5):156-159 (1985).
Ruddle, Nancy H. et al., "The Role of Lymphotoxin in Inflammation," *Prog. Allergy*, vol. 40:162-182 (1988).
Rudikoff, Stuart et al., "Functional antibody lacking a variable-region disulfide bridge," *Proc. Natl. Acad. Sci. USA*, vol. 83:7875-7878 (1986).
Rudikoff, Stuart et al., "Single amino acid substitution altering antigen-binding specificity," *Proc. Natl. Acad. Sci. USA*, vol. 79:1979-1983 (1982).
Sanchez, Anthony et al., "Analysis of Human Peripheral Blood Samples from Fatal and Nonfatal Cases of Ebola (Sudan) Hemorrhagic Fever: Cellular Responses, Virus Load, and Nitric Oxide Levels," *Journal of Virology*, vol. 78(19):10370-10377 (2004).
Sastry, K. Jagannadha et al., "HIV-1 *tat* Gene Induces Tumor Necrosis Factor-β (Lymphotoxin) in a Human B-lymphoblastoid Cell Line," *The Journal of Biological Chemistry*, vol. 265(33):20091-20093 (1990).
Sautès, Catherine et al., "Murine Soluble Fcγ Receptors/IgG-Binding Factors (IGG-BF): Analysis of the Relation to FcγRll and Production of Milligram Quantities of Biologically Active Recombinant IgG-BF," *Immunol. Res.*, vol. 11:181-190 (1992).
Sayegh, Mohamed H. et al., "CD28-B7 Blockade after Alloantigenic Challenge In Vivo Inhibits Th1 Cytokines but Spares Th2," *J. Exp. Med.*, vol. 181:1869-1874 (1995).
Scallon, Bernard J. et al., "Functional Comparisons of Different Tumour Necrosis Factor Receptor/IgG Fusion Proteins," *Cytokine*, vol. 7(8):759-770 (1995).
Schall, Thomas J. et al., "Molecular Cloning and Expression of a Receptor for Human Tumor Necrosis Factor," *Cell*, vol. 61:361-370 (1990).
Scheurich, Peter et al., "Immunoregulatory Activity of Recombinant Human Tumor Necrosis Factor (TNF)-α: Induction of TNF Receptors on Human T Cells and TNF-α-Mediated Enhancement of T Cell Responses," *The Journal of Immunology*, vol. 138(6):1786-1790 (1987).
Schiller, Joan H. et al., "Biological and Clinical Effects of Intravenous Tumor Necrosis Factor-α Administered Three Times Weekly," *Cancer Research*, vol. 51:1651-1658 (1991).
Schoenfeld, Hans-Joachim et al., "Efficient Purification of Recombinant Human Tumor Necrosis Factor β from *Escherichia coli* Yields Biologically Active Protein with a Trimeric Structure That Binds to Both Tumor Necrosis Factor Receptors," *The Journal of Biological Chemistry*, vol. 266(6):3863-3869 (1991).
Schriever, Folke et al., "The Central Role of Follicular Dendritic Cells in Lymphoid Tissues," *Advances in Immunology*, vol. 51:243-284 (1992).
Scott, Daryl A. et al., "The Pendred syndrome gene encodes a chloride-iodide transport system," *Nature Genetics*, vol. 21:440-443 (1999).
Séité, Paule et al., "BCL2 Gene Activation and Protein Expression in Follicular Lymphoma: a Report on 64 Cases," *Leukemia*, vol. 7(3):410-417 (1993).

Selmaj, Krzysztof et al., "Identification of Lymphotoxin and Tumor Necrosis Factor in Multiple Sclerosis Lesions," *J. Clin. Invest.*, vol. 87:949-954 (1991).
Shalaby, M. Rafaat et al., "The Involvement of Human Tumor Necrosis Factors-α and -β in the Mixed Lymphocyte Reaction," *The Journal of Immunology*, vol. 141(2):449-503 (1988).
Sheehan, Kathleen C.F. et al., "Generation and Characterization of Hamster Monoclonal Antibodies that Neutralize Murine Tumor Necrosis Factors," *The Journal of Immunology*, vol. 142(11):3884-3893 (1989).
Shehadeh, Naim N. et al., "Altered Cytokine Activity in Adjuvant Inhibition of Autoimmune Diabetes," *Journal of Autoimmunity*, vol. 6:291-300 (1993).
Sidman, Kenneth R. et al., "Controlled Release of Macromolecules and Pharmaceuticals from Synthetic Polypeptides Based on Glutamic Acid," *Biopolymers*, vol. 22:547-556 (1983).
Sigel, Morton B. et al., "Production of Antibodies by Inoculation into Lymph Nodes," *Methods in Enzymology*, vol. 93:3-12 (1983).
Simonet, W.S. et al., "Osteoprotegerin: A Novel Secreted Protein Involved in the Regulation of Bone Density," *Cell*, vol. 89:309-319 (1997).
Slepushkin, A.N. et al., "A comparative study of live and inactivated influenza vaccines: the organization of the observation and the results of a study of their reactogenicity and immunogenicity," *Vopr. Virusol.*, vol. 39(3):128-131 (1994).
Smith, Craig A. et al., "A Receptor for Tumor Necrosis Factor Defines an Unusual Family of Cellular and Viral Proteins," *Science*, vol. 248:1019-1023 (1990).
Smith, Craig A. et al., "CD30 Antigen, a Marker for Hodgkin's Lymphoma, is a Receptor Whose Ligand Defines an Emerging Family of Cytokines with Homology to TNF," *Cell*, vol. 73:1349-1360 (1993).
Smith, Craig A. et al., "The TNF Receptor Superfamily of Cellular and Viral Proteins: Actiyation, Costimulation, and Death," *Cell*, vol. 76(6):959-962 (1994).
Spriggs, David R. et al., "Tumor Necrosis Factor Expression in Human Epithelial Tumor Cell Lines," *J. Clin. Invest.*, vol. 81:455-460 (1988).
Stevenson, George T. et al., "Conjugation of Human Fcγ in Closed-Hinge or Open-Hinge Configuration to Fab'γ and Analogous Ligands," *The Journal of Immunology*, vol. 158:2242-2250 (1997).
Suda, Takashi et al., "Molecular Cloning and Expression of the Fas Ligand, a Novel Member of the Tumor Necrosis Factor Family," *Cell*, vol. 75:1169-1178 (1993).
Sureshkumar, G.K. et al., "The Influence of Temperature on a Mouse-Mouse Hybridoma Growth and Monoclonal Antibody Production," *Biotechnology and Bioengineering*, vol. 37:292-295 (1991).
Tartaglia, Louis A. et al., "Two TNF receptors," *Immunology Today*, vol. 13(5):151-153 (1992).
Tavernier, Jan et al., "Conserved residues of tumour necrosis factor and lymphotoxin constitute the framework of the trimeric structure," *FEBS*, vol. 257(2):315-318 (1989).
Tew, John G. et al., "Follicular Dendritic Cells as Accessory Cells," *Immunological Reviews*, vol. 117:185-211 (1990).
Thomas, H. et al., "Biological Approaches to Cancer Therapy," *The Journal of International Medical Research*, vol. 17:191-204 (1989).
Tibbetts, Randal S. et al., "Cardiac Antigen-Specific Autoantibody Production is Associated with Cardiomyopathy in Trypanosoma cruzi-infected mice," *Journal of Immunology*, vol. 152:1493-1499 (1994).
Toellner, Kai-Michael et al., "Immunoglobulin Swith Transcript Production In Vivo Related to the Site and Time of Antigen-specific B Cell Activation," *J. Exp. Med.*, vol. 183:2303-2312 (1996).
Traunecker, André et al., "Highly efficient neutralization of HIV with recombinant CD4-immunoglobulin molecules," *Nature*, vol. 339:68-70 (1989).
Trethewey, Pat, "Systemic Lupus Erythematosus," *Dimensions of Critical Care Nursing*, vol. 23(3):111-115 (2004).
Trüeb, Ralph et al., "Expression of an Adenovirally Encoded Lymphotoxin-β Inhibitor Prevents Clearance of *Listeria monocytogenes* in Mice," *Journal of Inflammation*, vol. 45:239-247 (1995).

Tschachler, Erwin et al., "Constitutive Expression of Lymphotoxin (Tumor Necrosis Factor β) in HTLV-I-Infected Cell Lines," *Human Retrovirology HTLV*, Raven Press, Ltd., William A. Blattner (Ed.), pp. 105-113 (1990).

Tsiagbe, V.K. et al., "Syngeneic Response to SJL Follicular Center B Cell Lymphoma (Reticular Cell Sarcoma) Cells is Primarily in Vβ16+ CD4+ T Cells," *The Journal of Immunology*, vol. 150:5519-5528 (1993).

Tsiagbe, V.K. et al., "The Physiology of Germinal Centers," *Critical Reviews in Immunology*, vol. 16:381-421 (1996).

Turner, Martin et al., "Human T cells from autoimmune and normal individuals can produce tumor necrosis factor," *Eur. J. Immunol.*, vol. 17:1807-1814 (1987).

Ullrich, Axel et al., "Signal Transduction by Receptors with Tyrosine Kinase Activity," *Cell*, vol. 61:203-212 (1990).

Van Dullemen, Hendrik M. et al., "Treatment of Crohn's Disease With Anti-Tumor Necrosis Factor Chimeric Monoclonal Antibody (cA2)," *Gastroenterology*, vol. 109:129-135 (1995).

Van Kooten, Cees et al., "CD40-CD40 Ligand: A Multifunctional Receptor—Ligand Pair," *Advances in Immunology*, vol. 61:1-77 (1996).

Van Vliet, Els et al., "Reticular Fibroblasts in Peripheral Lymphoid Organs Identified by a Monoclonal Antibody," *The Journal of Histochemistry and Cytochemistry*, vol. 34(7):883-890 (1986).

Ware, Carl F. et al., "Expression of Surface Lymphotoxin and Tumor Necrosis Factor on Activated T, B, and Natural Killer Cells," *The Journal of Immunology*, vol. 149(12):3881-3888 (1992).

Ware, Carl F. et al., "Human T Cell Hybridomas Producing Cytotoxic Lymphokines: Induction of Lymphotoxin Release and Killer Cell Activity by Anti-CD3 Monoclonal Antibody or Lectins and Phorbol Ester," *Lymphokine Research*, vol. 5(4):313-324 (1986).

Ware, Carl F. et al., "Mechanisms of Lymphocyte-mediated Cytotoxicity II. Biochemical and Serologic Identification of a Precursor Lymphotoxin Form (pre-LT) Produced by MLC-Sensitized Human T Lymphocytes In Vitro," *The Journal of Immunology*, vol. 126(5):1927-1933 (1981).

Ware, Carl F. et al., "Regulation of the CTL Lytic Pathway by Tumor Necrosis Factor," *Cellular Immunity and the Immunotherapy of Cancer*, pp. 121-128 (1990).

Ware, C.F. et al., "The Ligands and Receptors of the Lymphotoxin System," *Curr. Top. Microbiol. Immunol.*, vol. 198:175-218 (1995).

Warfield, Kelly L. et al., "Induction of Humoral and CD8+ T Cell Responses Are Required for Protection against Lethal Ebola Virus Infection," *The Journal of Immunology*, vol. 175:1184-1191 (2005).

Warzocha, Krzysztof et al., "Mechanisms of action of the tumor necrosis factor and lymphotoxin ligand-receptor system," *Eur. Cytokine Netw.*, vol. 5(6):83-96 (1994).

Watanabe-Fukunaga, Rie et al., "Lymphoproliferation disorder in mice explained by defects in Fas antigen that mediates apoptosis," *Nature*, vol. 356:314-317 (1992).

Weickert, Michael J. et al., "Stabilization of Apoglobin by Low Temperature Increases Yield of Soluble Recombinant Hemoglobin in *Escherichia coli*," *Applied and Environmental Microbiology*, vol. 63(11):4313-4320 (1997).

Weidemann, Ralf et al., "Low temperature cultivation—a step towards process optimisation," *Cytotechnology*, vol. 15:111-126 (1994).

Williams, Richard O. et al., "Successful therapy of collagen-induced arthritis with TNF receptor-IgG fusion protein and combination with anti-CD4," *Immunology*, vol. 84:433-439 (1995).

Winter, Greg et al., "Man-made antibodies," *Nature*, vol. 349:293-299 (1991).

Wong, G.H.W. et al., "Strategies for Manipulating Apoptosis for Cancer Therapy With Tumor Necrosis Factor and Lymphotoxin," *Journal of Cellular Biochemistry*, vol. 60:56-60 (1996).

Wong, Grace H.W. et al., "Tumour necrosis factor α and β inhibit virus replication and synergize with interferons," *Nature*, vol. 323:819-822 (1986).

Wu, Qiang et al., "The Requirement of Membrane Lymphotoxin for the Presence of Dendritic Cells in Lymphoid Tissues," *J. Exp. Med.*, vol. 190(5):629-638 (1999).

Wysocki, L.J. et al., "'Panning' for lymphocytes: A method for cell selection," *Proc. Natl. Acad. Sci. USA*, vol. 75(6):2844-2848 (1978).

Xu, Jianchao et al., "Mice Deficient for teh CD40 Ligand," *Immunity*, vol. 1:423-431 (1994).

Yonehara, Shin et al., "A Cell-killing monoclonal antibody (Anti-Fas) to a Cell Surface Antigen Co-downregulated with the Receptor of Tumor Necrosis Factor," *J. Exp. Med.*, vol. 169:1747-1756 (1989).

Zhai, Yifan et al., "Light, a Novel Ligand for Lymphotoxin β Receptor and TR2/HVEM Induces Apoptosis and Suppresses in Vivo Tumor Formation Via Gene Transfer," *J. Clin. Invest.*, vol. 102(6):1142-1151 (1998).

Zhou, M. et al., "Real-Time Measurements of Kinetics of EGF Binding to Soluble EGF Receptor Monomers and Dimers Support the Dimerization Model for Receptor Activation," *Biochemistry*, vol. 32:8193-8198 (1993).

Ziff, Morris, "Emigration of Lymphocytes in Rheumatoid Synovitis," *Advances in Inflammation Research*, vol. 12:1-9 (1988).

International Search Report for Application No. PCT/US2007/081761, dated Aug. 25, 2008.

International Preliminary Report on Patentability for Application No. PCT/US2007/081761, dated Apr. 22, 2009.

* cited by examiner

SEQUENCE LISTING

```
<160> NUMBER OF SEQ ID NOS: 11

<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ala Val Pro Pro Tyr
            20                  25                  30

Ala Ser Glu Asn Gln Thr Cys Arg Asp Gln Glu Lys Glu Tyr Tyr Glu
        35                  40                  45
```

Pro Gln His Arg Ile Cys Cys Ser Arg Cys Pro Pro Gly Thr Tyr Val
    50                  55                  60

Ser Ala Lys Cys Ser Arg Ile Arg Asp Thr Val Cys Ala Thr Cys Ala
65                  70                  75                  80

Glu Asn Ser Tyr Asn Glu His Trp Asn Tyr Leu Thr Ile Cys Gln Leu
                85                  90                  95

Cys Arg Pro Cys Asp Pro Val Met Gly Leu Glu Glu Ile Ala Pro Cys
            100                 105                 110

Thr Ser Lys Arg Lys Thr Gln Cys Arg Cys Gln Pro Gly Met Phe Cys
        115                 120                 125

Ala Ala Trp Ala Leu Glu Cys Thr His Cys Glu Leu Leu Ser Asp Cys
130                 135                 140

Pro Pro Gly Thr Glu Ala Glu Leu Lys Asp Glu Val Gly Lys Gly Asn
145                 150                 155                 160

Asn His Cys Val Pro Cys Lys Ala Gly His Phe Gln Asn Thr Ser Ser
                165                 170                 175

Pro Ser Ala Arg Cys Gln Pro His Thr Arg Cys Glu Asn Gln Gly Leu
            180                 185                 190

Val Glu Ala Ala Pro Gly Thr Ala Gln Ser Asp Thr Thr Cys Lys Asn
        195                 200                 205

Pro Leu Glu Pro Leu Pro Pro Glu Met Ser Gly Thr Met Val Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 2
<211> LENGTH: 435
<212> TYPE: PRT

<213> ORGANISM: Homo sapiens

<400> SEQUENCE: 2

```
Met Leu Leu Pro Trp Ala Thr Ser Ala Pro Gly Leu Ala Trp Gly Pro
1               5                   10                  15

Leu Val Leu Gly Leu Phe Gly Leu Leu Ala Ala Ser Gln Pro Gln Ala
            20                  25                  30

Val Pro Pro Tyr Ala Ser Glu Asn Gln Thr Cys Arg Asp Gln Glu Lys
        35                  40                  45

Glu Tyr Tyr Glu Pro Gln His Arg Ile Cys Cys Ser Arg Cys Pro Pro
    50                  55                  60

Gly Thr Tyr Val Ser Ala Lys Cys Ser Arg Ile Arg Asp Thr Val Cys
65                  70                  75                  80

Ala Thr Cys Ala Glu Asn Ser Tyr Asn Glu His Trp Asn Tyr Leu Thr
                85                  90                  95

Ile Cys Gln Leu Cys Arg Pro Cys Asp Pro Val Met Gly Leu Glu Glu
            100                 105                 110

Ile Ala Pro Cys Thr Ser Lys Arg Lys Thr Gln Cys Arg Cys Gln Pro
        115                 120                 125

Gly Met Phe Cys Ala Ala Trp Ala Leu Glu Cys Thr His Cys Glu Leu
130                 135                 140

Leu Ser Asp Cys Pro Pro Gly Thr Glu Ala Glu Leu Lys Asp Glu Val
145                 150                 155                 160

Gly Lys Gly Asn Asn His Cys Val Pro Cys Lys Ala Gly His Phe Gln
                165                 170                 175

Asn Thr Ser Ser Pro Ser Ala Arg Cys Gln Pro His Thr Arg Cys Glu
            180                 185                 190

Asn Gln Gly Leu Val Glu Ala Ala Pro Gly Thr Ala Gln Ser Asp Thr
        195                 200                 205

Thr Cys Lys Asn Pro Leu Glu Pro Leu Pro Pro Glu Met Ser Gly Thr
210                 215                 220

Met Leu Met Leu Ala Val Leu Leu Pro Leu Ala Phe Phe Leu Leu Leu
225                 230                 235                 240

Ala Thr Val Phe Ser Cys Ile Trp Lys Ser His Pro Ser Leu Cys Arg
                245                 250                 255

Lys Leu Gly Ser Leu Leu Lys Arg Arg Pro Gln Gly Glu Gly Pro Asn
            260                 265                 270

Pro Val Ala Gly Ser Trp Glu Pro Pro Lys Ala His Pro Tyr Phe Pro
        275                 280                 285

Asp Leu Val Gln Pro Leu Leu Pro Ile Ser Gly Asp Val Ser Pro Val
    290                 295                 300

Ser Thr Gly Leu Pro Ala Ala Pro Val Leu Glu Ala Gly Val Pro Gln
305                 310                 315                 320

Gln Gln Ser Pro Leu Asp Leu Thr Arg Glu Pro Gln Leu Glu Pro Gly
                325                 330                 335

Glu Gln Ser Gln Val Ala His Gly Thr Asn Gly Ile His Val Thr Gly
            340                 345                 350

Gly Ser Met Thr Ile Thr Gly Asn Ile Tyr Ile Tyr Asn Gly Pro Val
        355                 360                 365

Leu Gly Gly Pro Pro Gly Pro Gly Asp Leu Pro Ala Thr Pro Glu Pro
    370                 375                 380

Pro Tyr Pro Ile Pro Glu Glu Gly Asp Pro Gly Pro Pro Gly Leu Ser
385                 390                 395                 400

Thr Pro His Gln Glu Asp Gly Lys Ala Trp His Leu Ala Glu Thr Glu
```

```
                    405                 410                 415
His Cys Gly Ala Thr Pro Ser Asn Arg Gly Pro Arg Asn Gln Phe Ile
                420                 425                 430

Thr His Asp
    435

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctggcatgga gagtgtggta                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatacgtcaa gcccctcaag                                                  20

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtactctgcc agcctggcac agaagccgag gtcacagatg                             40

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtatggggt tgacagcggg ctcgagggga gg                                    32

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
acgtcaactg tgtccc                                                      16

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
                                    primer

<400> SEQUENCE: 8
gctgctggca ccagactt                                                      18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggctaccac atccaagg                                                      18

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
caaattaccc actcccgacc cg                                                 22

<210> SEQ ID NO 11
<211> LENGTH: 194
<212> TYPE: PRT
<213> ORGANISM: Homo sapiens

<400> SEQUENCE: 11

Ala Val Pro Pro Tyr Ala Ser Glu Asn Gln Thr Cys Arg Asp Gln Glu
1               5                   10                  15

Lys Glu Tyr Tyr Glu Pro Gln His Arg Ile Cys Cys Ser Arg Cys Pro
            20                  25                  30

Pro Gly Thr Tyr Val Ser Ala Lys Cys Ser Arg Ile Arg Asp Thr Val
        35                  40                  45

Cys Ala Thr Cys Ala Glu Asn Ser Tyr Asn Glu His Trp Asn Tyr Leu
    50                  55                  60

Thr Ile Cys Gln Leu Cys Arg Pro Cys Asp Pro Val Met Gly Leu Glu
65                  70                  75                  80

Glu Ile Ala Pro Cys Thr Ser Lys Arg Lys Thr Gln Cys Arg Cys Gln
                85                  90                  95

Pro Gly Met Phe Cys Ala Ala Trp Ala Leu Glu Cys Thr His Cys Glu
            100                 105                 110

Leu Leu Ser Asp Cys Pro Pro Gly Thr Glu Ala Glu Leu Lys Asp Glu
        115                 120                 125

Val Gly Lys Gly Asn Asn His Cys Val Pro Cys Lys Ala Gly His Phe
    130                 135                 140

Gln Asn Thr Ser Ser Pro Ser Ala Arg Cys Gln Pro His Thr Arg Cys
145                 150                 155                 160

Glu Asn Gln Gly Leu Val Glu Ala Ala Pro Gly Thr Ala Gln Ser Asp
                165                 170                 175

Thr Thr Cys Lys Asn Pro Leu Glu Pro Leu Pro Pro Glu Met Ser Gly
            180                 185                 190

Thr Met
```

TREATMENT OF DEMYELINATING DISORDERS WITH SOLUBLE LYMPHOTOXIN-β-RECEPTOR

BACKGROUND

Lymphotoxin beta receptor (LTβR) is a member of the tumor necrosis factor receptor (TNFR) family. The receptor is expressed on the surface of cells in the parenchyma and stroma of most lymphoid organs but is absent on T- and B-lymphocytes. Signaling through LTβR by the LTα/β heterotrimer (LT) is important during lymphoid development. LTβR is also known to bind the ligand LIGHT (homologous to lymphotoxins, exhibits inducible expression, and competes with herpes simplex virus glycoprotein D for HVEM, a receptor expressed by T lymphocytes), which has been implicated in T-cell driven events, both in the periphery and in the thymus. LT and LIGHT are expressed on the surface of activated lymphocytes. Blocking the LT pathway with a soluble decoy LTβR has been shown to be effective to treat autoimmune disease in various animal models.

SUMMARY

The invention is based, in part, on the discovery that a soluble form of LTβR (e.g., LTβR-Fc) can effectively promote remyelination in a subject. Accordingly, the invention provides methods, compositions (e.g., a soluble LTβR fusion protein, e.g., LTβR-Fc), devices, and kits useful for treating a demyelinating disorder (e.g., Multiple Sclerosis) in a subject, as well as for monitoring remyelination in the subject.

In one aspect, the invention features a method of treating a demyelinating disorder in a subject. The method includes the steps of: (i) administering to a subject a dose of a soluble LTβR (e.g., an LTβR fusion protein such as LTβR-Fc) sufficient to promote remyelination; and optionally (ii) monitoring the subject for remyelination. Optionally, the method can also include the step of identifying a subject (e.g., a human (e.g., a human patient)) as one having, or at risk of developing, a demyelinating disorder.

In some embodiments, the method can include the step of selecting a subject (e.g., a human patient) on the grounds that the subject is in need of remyelination.

In some embodiments, the method can also include the step of classifying the subject (e.g., the human patient) as being in need of remyelination.

In some embodiments, the method can further include the step of classifying the subject (e.g., the human patient) as having a preselected level of remyelination, e.g., no remyelination or having some level of remyelination. Preferably, the patient is classified as having remyelination, e.g., the patient is classified as having a preselected level, e.g., a level selected from a set of graduated levels of remyelination, e.g., a minimal, intermediate, or larger amount of remyelination. The graduated level or amount of remyelination can also be expressed or assigned as a discreet value, e.g., a scale of ascending values, e.g., 1-10, wherein a first score, e.g., a first score of "10," indicates more remyelination in a patient than one having a second, lower score, e.g., a second score of "9." The classification can be performed once or more than once. It may be desirable to classify a patient after a first preselected milestone, e.g., a preselected number of administrations, a predetermined period of treatment, or a preselected level of an increase or diminution of one or more symptoms. Classification can, optionally, be performed again at a second or subsequent milestone, e.g., a milestone of the same type. In a related embodiment, a record of the classification (e.g., the preselected level of remyelination) of the subject is made, e.g., a computer readable record.

In some embodiments, the subject is treated with a soluble LTβR (e.g., an LTβR fusion polypeptide such as LTβR-Fc). In some embodiments, the soluble LTβR is an LTβR-Fc fusion polypeptide having the amino acid sequence depicted in SEQ ID NO:1 (see below).

The subject can be any mammal including, for example, a mouse, a rabbit, a guinea pig, a monkey, or a human (e.g., a human patient). The subject (e.g., a human patient) can be any subject having, or at risk of developing a demyelinating disorder. As used herein, a "demyelinating disorder" is any disease associated with the destruction or removal of myelin, the fatty sheath surrounding and insulating nerve fibers, from nerves. Demyelinating disorders include, for example, Multiple Sclerosis (e.g., Relapsing/Remitting Multiple Sclerosis, Secondary Progressive Multiple Sclerosis, Progressive Relapsing Multiple Sclerosis, Primary Progressive Multiple Sclerosis, and Acute Fulminant Multiple Sclerosis), Central Pontine Myelinolysis, Acute Disseminated Encephalomyelitis, Progressive Multifocal Leukoencephalopathy; Subacute Sclerosing Panencephalitis, Post-infectious Encephalomyelitis, Chronic Inflammatory Demyelinating Polyneuropathy, Guillain-Barre Syndrome, Progressive Multifocal Leucoencephalopathy, Devic's Disease, Balo's Concentric Sclerosis, and a leukodystrophy (e.g., Metachromatic Leukodystrophy, Krabbé disease, Adrenoleukodystrophy, Pelizaeus-Merzbacher disease, Canavan disease, Childhood Ataxia with Central Hypomyelination, Alexander disease, or Refsum disease). A human patient having a demyelinating disorder can have one or more symptoms of a demyelinating disorder such as, but not limited to, impaired vision, numbness, weakness in extremities, tremors or spasticity, heat intolerance, speech impairment, incontinence, dizziness, or impaired proprioception (e.g., balance, coordination, sense of limb position). A human (e.g., a human patient) with a family history of a demyelinating disorder (e.g., a genetic predisposition for a demyelinating disorder), or who exhibits mild or infrequent symptoms of a demyelinating disorder described above can be, for the purposes of the method, considered at risk of developing a demyelinating disorder (e.g., Multiple Sclerosis).

In some embodiments, the soluble LTβR can be administered to the subject in an amount, frequency, and/or for a time sufficient to induce remyelination in the subject.

In some embodiments, for the purpose of inducing remyelination in a subject, the soluble LTβR (e.g., a LTβR fusion polypeptide such as LTβR-Fc) is administered to the subject once. In other embodiments, the soluble LTβR (e.g., a LTβR fusion polypeptide such as LTβR-Fc) is administered to the subject more than once, e.g., once every 3-10 days; at least twice and not more than once every 5-20 days; at least twice and not more than once every 28-31 days; weekly; biweekly; monthly; weekly over the course of at least 4 weeks; biweekly over the course of at least 6 weeks; monthly over the course of at least 3 months; or monthly over the course of at least 6 months.

In some embodiments, a suitable starting dose of soluble LTβR in trials to determine a dosage (e.g., the amount sufficient to induce remyelination in a subject) is 0.001 mg of soluble LTβR per kg body weight of the subject.

In some embodiments, a suitable dose or starting dose is determined by a number of subjective, patient-specific factors such as, but not limited to, sex, age, weight, physical health, or any other factor described herein.

In some embodiments, the soluble LTβR (e.g., an LTβR fusion polypeptide such as LTβR-Fc) is administered to a subject intravenously or parenterally (e.g., subcutaneously, intramuscularly, intranasally, or orally).

In some embodiments, the soluble LTβR (e.g., an LTβR fusion polypeptide such as LTβR-Fc) can be administered to a subject as a monotherapy.

In some embodiments, the soluble LTβR (e.g., an LTβR fusion polypeptide such as LTβR-Fc) can be administered to a subject as a combination therapy with another treatment, e.g., another treatment for a demyelinating disorder (e.g., any of the demyelinating disorders described herein (e.g., Multiple Sclerosis)). For example, the combination therapy can include administering to the subject (e.g., a human patient) one or more additional agents that provide a therapeutic benefit to the subject who has, or is at risk of developing, a demyelinating disorder. In some embodiments, the soluble LTβR and the one or more additional agents are administered at the same time. In other embodiments, the soluble LTβR is administered first in time and the one or more additional agents are administered second in time. In some embodiments, the one or more additional agents are administered first in time and the soluble LTβR is administered second in time. The soluble LTβR can replace or augment a previously or currently administered therapy. For example, upon treating with LTβR, administration of the one or more additional agents can cease or diminish, e.g., be administered at lower levels. In other embodiments, administration of the previous therapy is maintained. In some embodiments, a previous therapy will be maintained until the level of LTβR reaches a level sufficient to provide a therapeutic effect. The two therapies can be administered in combination.

In some embodiments, a human receiving a first therapy for a demyelinating disorder (e.g., Multiple Sclerosis), e.g., Interferon Beta 1a (Avonex), Interferon Beta 1b (Rebif), glatiramer acetate (Copaxone), mitoxantrone (Novantrone), azathiprine (Imuran), cyclophosphamide (Cytoxan or Neosar), cyclosporine (Sandimmune), methotrexate, Cladribine (Leustatin), methylprednisone (Depo-Medrol or Solu-Medrol), prednisone (Deltasone), prednisolone (Delta-Cortef), dexamethasone (Medrol or Decadron), adreno-corticotrophic hormone (ACTH), or Corticotropin (Acthar), can also be administered a soluble LTβR, e.g., LTβR-Fc. In some embodiments, when the human is administered the soluble LTβR, the first therapy is halted. In other embodiments, the human is monitored for a first pre-selected result, e.g., an improvement in one or more symptoms of a demyelinating disorder (such as increased remyelination), e.g., any of the symptoms of demyelinating disorders described herein. In some embodiments, when the first pre-selected result is observed, treatment with the soluble LTβR is decreased or halted. In some embodiments, the human is then monitored for a second pre-selected result after treatment with the soluble LTβR is halted, e.g., a worsening of a symptom of a demyelinating disorder. When the second pre-selected result is observed, administration of the soluble LTβR to the human is reinstated or increased, or administration of the first therapy is reinstated, or the human is administered both a soluble LTβR, or an increased amount of soluble LTβR, and the first therapeutic regimen.

In one embodiment, a human receiving a first therapy for a demyelinating disorder (e.g., Multiple Sclerosis or any other demyelinating disorder described herein), who is then treated with a soluble LTβR, e.g., an LTβR-Fc, continues to receive the first therapy at the same or a reduced amount. In another embodiment, treatment with the first therapy overlaps for a time with treatment with the soluble LTβR, but treatment with the first therapy is subsequently halted.

In some embodiments, the soluble LTβR can be administered to a subject receiving an anti-TNF therapy (e.g., Humira, Enbrel, or Remicade). In some embodiments, the subject receiving the anti-TNF therapy has an autoimmune disorder such as, but not limited to, rheumatoid arthritis.

Monitoring a subject (e.g., a human patient) for remyelination, as defined herein, means evaluating the subject for a change, e.g., an improvement in one or more parameters that are indicative of remyelination, e.g., one can monitor improvement in one or more symptoms of a demyelinating disorder. Such symptoms include any of the symptoms of a demyelinating disorder described herein. Remyelination can also be monitored by methods which include direct determination of the state of myelin in the subject, e.g., one can measure white matter mass using magnetic resonance imaging (MRI) or measure the thickness of myelin fibers using a magnetic resonance spectroscopy (MRS) brain scan. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration, preferably the first administration, of the soluble LTβR. The subject can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic Modality, e.g., adding or dropping any of the treatments for demyelinating disorders described herein. For example, continued administration of the soluble LTβR could be done with one or more additional treatment agents where necessary. In a preferred embodiment, if a preselected outcome of the evaluation is obtained, an additional step is taken, e.g., the subject is administered another treatment or another evaluation or test is performed. The level of remyelination can be used to make a determination on patient care, e.g., a selection or modification of a course of treatment or the decision of a third party to reimburse for the treatment.

In some embodiments, monitoring a subject (e.g., a human patient) for remyelination can also include monitoring for a reduction in the size or number of inflammatory lesions (i.e., scleroses) using, e.g., Magnetic Resonance Imaging (MRI) scans, Positron-Emission Tomography (PET) scans, Diffusion-Weighted Imaging (DW-I, or DW-MRI), Diffusion Tensor Imaging, Myelography, Magnetization Transfer. In some embodiments, monitoring a subject for remyelination can include the detection in cerebrospinal fluid of the presence of, e.g., (i) abnormal proteins such as tiny fragments of myelin, (ii) elevated levels of or specific types of lymphocytes, and/or (iii) abnormal levels of immunoglobulin (IgG) molecules; the fluid obtained from a lumbar puncture (i.e., a spinal tap). In other embodiments, monitoring a subject for remyelination can include assessment of a change in the subject's neuropsychology (e.g., the status of various abilities such as memory, arithmetic, attention, judgment and reasoning). In some embodiments, the monitoring of a subject (e.g., a human patient) for remyelination can involve testing a patient's urine for a decrease in levels of myelin basic protein-like material (MBPLM), which substance becomes elevated as axonal damage occurs during disease progression. In some embodiments, where the demyelinating disorder affects a subject's eyes or vision, the monitoring of a subject for remyelination can involve testing for improvements in, e.g., color blindness.

In one aspect, the disclosure features a method of evaluating a subject, to determine, e.g., if a subject is responding or not responding to a treatment for a demyelinating disorder, e.g., a therapy that increases remyelination in a subject such as administering a soluble LTβR. The method includes providing a reference value (e.g., a pre-administration value) for the level or state of myelin in the subject, and optionally, administering to the subject a medicament that increases remyelination (e.g., a soluble LTβR, e.g., an LTβR fusion polypeptide such as LTβR-Fc). In embodiments where a medicament is administered, the method also includes providing a post-administration value for the level or state of myelin in the subject (e.g., the level or state of myelin following administration of a remyelination therapy) and comparing the post-administration value with the reference value, thereby evaluating the subject, e.g., determining if the subject is responding or not responding to the therapy. The post-administration value (i.e., the value corresponding to the state or level of myelin in a subject following a remyelination therapy) can be determined, e.g., by any of the assessment methods described herein. The reference value (i.e., the state or level of myelin in a subject prior to treatment with a remyelination therapy) can also be determined, e.g., by any of the assessment methods described herein.

In some embodiments, the method includes assigning the subject to a class, and optionally, recording the assignment, e.g., in a computer readable record.

In some embodiments, the evaluation includes determining if the subject is responding. In other embodiments, the evaluation includes determining if the subject is not responding.

In some embodiments, the evaluation includes providing information on which to make a decision about the subject.

In some embodiments, the method further includes the step of selecting the subject for a preselected treatment.

In some embodiments, the method further includes the step of selecting a duration of treatment of demyelinating disorder (e.g., Multiple Sclerosis) in a subject.

In some embodiments, a determination that a subject is responding indicates that a shorter duration of treatment can/should/will be/is administered to the subject (e.g., shorter than the treatment which is recommended for a subject who is not responding to a therapy, or a duration shorter than currently used with existing therapies for demyelinating disorders, and optionally, that indication is entered into a record.

In some embodiments, a determination that a subject is responding indicates that a shorter duration of treatment is counter-indicated for the subject (e.g., a duration shorter than currently used with existing treatments for demyelinating disorders, e.g., any of the treatments for demyelinating disorders described herein), and optionally, that indication is entered into a record.

In some embodiments, providing a comparison of the post-administration value with a reference value includes: providing a determination of a post-administration level of myelin in a subject at a first time point (e.g., wherein the first time point is 6, 7, 8, 9, 10, 11, 12, 13, 14 or more days (e.g., 3, 4, 5, 6, 8 or more weeks (e.g., 3, 4, 6, 12 or more months))) after the commencement of administration of the remyelination therapy (e.g., a soluble LTβR)); providing a determination of a reference value of the state or level of myelin in the subject at a second time point that is prior to the first time point (e.g., wherein the second time point is prior to, or within about 1, 2, 3, 4, or 5 days of the commencement of, administration of a remyelination therapy (e.g., a soluble LTβR, e.g., LTβR-Fc); and providing a comparison of the post administration level and reference value of a subject's myelin, wherein increased levels of myelin in a subject (e.g., the levels differ by no more than about 60%, about 50%, about 40%, about 30%, about 20%, about 10%, about 5%, about 2%, or about 1%) between the post-administration level and reference value indicates that the subject is responding.

In another aspect, the invention features a method of selecting a payment class for a course of treatment with a remyelination therapy (e.g., a soluble LTβR an LTβR fusion polypeptide such as LTβR-Fc) for a patient having a demyelinating disorder, e.g., Multiple Sclerosis. The method includes providing (e.g., receiving) an evaluation of whether the patient is responding or not responding to a therapy for a demyelinating disorder; and performing at least one of (1) if the patient is responding (e.g., remyelination occurs in the patient), selecting a first payment class, and (2) if the subject is not responding (e.g., no remyelination in the patient), selecting a second payment class. The therapy can include a soluble LTβR (e.g., an LTβR fusion polypeptide such as LTβR-Fc). The therapy can also include one or more of any of the therapies for demyelinating disorders described herein. In some embodiments, the therapy is one that increases remyelination in a patient such as a soluble LTβR.

In some embodiments, assignment of the patient is to the first payment class and the assignment authorizes payment for a course of treatment for a first duration. In some embodiments, the patient is responding to a therapy for a demyelinating disorder and a treatment duration of less than 52, 48, 36, 24, 18, 12, 10, 8, 4 or 2 weeks is authorized.

In some embodiments, assignment of the patient is to the second payment class and the assignment authorizes payment for a course of treatment for a second duration. In some embodiments, the patient is not responding to a therapy for a demyelinating disorder and a treatment duration of more than 52, 48, 36, 24, 18, 12, 10, 8, 4 or 2 weeks is authorized.

In some embodiments, the determination of whether a patient is responding to a therapy is made by evaluating the subject for a change, an improvement, in one or more parameters that are indicative of remyelination, e.g., one can monitor improvement in one or more symptoms of a demyelinating disorder. Such symptoms include any of the symptoms of a demyelinating disorder described herein. Remyelination can also be monitored by methods which include direct determination of the state of myelin in the subject, e.g., one can measure white matter mass using magnetic resonance imaging (MRI), measure the thickness of myelin fibers using a magnetic resonance spectroscopy (MRS) brain scan, or any other direct measures described herein.

In another embodiment, the determination of whether a patient is responding to a therapy can also be evaluated by any other assessment or indicia described herein, including, but not limited to, monitoring a patient for a reduction in the size or number of inflammatory lesions (i.e., scleroses) present in the patient; monitoring a patient's cerebrospinal fluid for a reduction in the presence or amount of, e.g., (i) abnormal proteins such as tiny fragments of myelin, (ii) elevated levels of or specific types of lymphocytes, and/or (iii) abnormal levels of immunoglobulin (IgG) molecules; monitoring a patient for a positive change in neuropsychology (e.g., the status of various abilities such as memory, arithmetic, attention, judgment and reasoning); and/or monitoring a patient's urine for a decrease in levels of myelin basic protein-like material (MBPLM).

In some embodiments, at least a 5% (e.g., at least 10%, at least 15%, at least 20%, at least 25%, at least 30%, at least 35%, at least 40%, at least 50%, at least 60%, at least 70%) improvement in one or more symptoms of a demyelinating disorder or other above-described indicia following a remyelination therapy (e.g., a therapy that induces remyelination in a subject, e.g., a therapy such as a soluble LTβR) is sufficient to classify the patient as responding to a therapy.

In another aspect, the invention features a method of providing information on which to make a decision about a human subject (e.g., a patient), or making such a decision. The method includes providing (e.g., receiving) an evaluation of a patient, wherein the evaluation was made by a method described herein, e.g., determining if a patient has, or is at risk of developing, a demyelinating disorder or is one in need of, or likely to benefit from, increased remyelination; providing a determination of a post-administration state, level, or amount of myelin in a patient (e.g., the extent of remyelination); thereby providing a post-administration value; providing a comparison of the post-administration level with a reference value (e.g., the level of myelin present in a patient prior to treatment); and thereby, providing information on which to make a decision about a patient, or making such a decision.

In some embodiments, the method includes making the decision about the patient.

In some embodiments, the method also includes communicating the information to another party (e.g., by computer, compact disc, telephone, facsimile, email, or letter).

In some embodiments, the method includes recording the information, e.g., in a computer readable record or in a patient's file.

In some embodiments, the decision includes selecting a patient for payment, making or authorizing payment for a first course of action if the subject is responding to a therapy for a demyelinating disorder (e.g., a therapy that increases remyelination in a patient) and a second course of action if the patient is not responding to a therapy for a demyelinating disorder.

In some embodiments, the decision includes selecting a first course of action if the post-administration value has a first predetermined relationship with a reference value (e.g., the post-administration value is higher than the reference value), and selecting a second course of action if the post administration value has a second predetermined relationship with the reference value (e.g., the post-administration value is lower than the reference value).

In some embodiments, the decision includes selecting a first course of action if the patient is responding and a second course of action if the subject is not responding to a therapy for a demyelinating disorder (e.g., a therapy that increases remyelination in a patient).

In some embodiments, the patient is responding and the course of action is authorization of a course of therapy. In some embodiments, the course of therapy is shorter than what is provided to an otherwise similar patient who is not responding, e.g., the course of therapy is less than 52, 48, 36, 24, 18, 12, 10, 8, 4 or 2 weeks.

In some embodiments, the patient is responding to a therapy and the course of action is assigning the patient to a first class. In some embodiments, assignment to the first class will enable payment for a treatment provided to the patient. In some embodiments, payment is by a first party to a second party. In some embodiments, the first party is other than the patient. In some embodiments, the first party is selected from a third party payor, an insurance company, employer, employer sponsored health plan, HMO, or governmental entity. In some embodiments, the second party is selected from the subject, a healthcare provider, a treating physician, an HMO, a hospital, a governmental entity, or an entity which sells or supplies the drug. In some embodiments, the first party is an insurance company and the second party is selected from the patient, a healthcare provider, a treating physician, an HMO, a hospital, a governmental entity, or an entity which sells or supplies the drug. In some embodiments, the first party is a governmental entity and the second party is selected from the patient, a healthcare provider, a treating physician, an HMO, a hospital, an insurance company, or an entity which sells or supplies the drug.

In some embodiments, the patient is not responding and the course of action is authorization of a course of therapy. In some embodiments, the course of therapy is longer than what is provided to an otherwise similar patient who is responding to a therapy for a demyelinating disorder (e.g., a therapy that increases remyelination in a subject), e.g., the course of therapy is longer than 52, 48, 36, 24, 18, 12, 10, 8, 4 or 2 weeks. In some embodiments, the subject is not responding and the course of action is assigning the patient to a second class. In some embodiments, assignment to the second class will enable payment for a treatment provided to the patient, e.g., treatment for a period which is longer than a preselected period (e.g., longer than the period of treatment for an enhanced responder). In some embodiments, payment is by a first party to a second party. In some embodiments, the first party is other than the patient. In some embodiments, the first party is selected from a third party payor, an insurance company, employer, employer sponsored health plan, HMO, or governmental entity. In some embodiments, the second party is selected from the subject, a healthcare provider, a treating physician, an HMO, a hospital, a governmental entity, or an entity which sells or supplies the drug. In some embodiments, the first party is an insurance company and the second party is selected from the subject, a healthcare provider, a treating physician, an HMO, a hospital, a governmental entity, or an entity which sells or supplies the drug. In some embodiments, the first party is a governmental entity and the second party is selected from the subject, a healthcare provider, a treating physician, an HMO, a hospital, an insurance company, or an entity which sells or supplies the drug.

In some embodiments, the patient is one having, or at risk of developing, a demyelinating disorder such as Multiple Sclerosis or any other demyelinating disorder described herein.

In another aspect, the disclosure features a method of selecting a payment class for a course of treatment with a remyelination therapy for a subject having, or at risk of developing, a demyelinating disorder and/or a subject in need of, or likely to benefit from, increased remyelination. The method includes identifying the subject as one responding to the therapy, and approving, making, authorizing, receiving, transmitting or otherwise allowing payment of a selected course of treatment, e.g., a shorter course of treatment (e.g., less than 52, 48, 36, 24, 18, 12, 10, 8, 4 or 2 weeks) than if the subject has been identified as not responding to a therapy.

In another aspect, the invention features a method of treating a demyelinating disorder in a human, which includes the steps of administering to a subject (e.g., a human (e.g., a human patient)) a dose of a soluble LTβR (e.g., a LTβR fusion polypeptide such as LTβR-Fc), where said administration is sufficient such that remyelination occurs in the human. The method can optionally include the step of identifying a subject as one having, or at risk of developing, a demyelinating disorder. The method can also, optionally, include the step of monitoring the subject for remyelination. The subject can be any subject described herein. The demyelinating disorder can be any demyelinating disorder described herein (e.g., Multiple Sclerosis). The soluble LTβR can be any of those described herein. Administration of the soluble LTβR to a subject can include any of the routes, doses, or schedules described herein (e.g., see any of the administration methods described above). In some embodiments, the soluble LTβR (e.g., an LTβR fusion polypeptide such as LTβR-Fc) can be administered as a monotherapy or in combination with one or more additional therapies for a demyelinating disorder as described above. In some embodiments, the soluble LTβR can be administered to a subject receiving an anti-TNF therapy (e.g., Humira, Enbrel, or Remicade). A subject can be identified as one having, or at risk of developing, a demyelinating disorder using any of the methods described herein. Monitoring a subject (e.g., a human patient) for remyelination can include any of the methods described herein.

In another aspect, the invention features a method of treating a demyelinating disorder in a human, which includes the steps of: (i) administering to a human a dose of a soluble LTβR sufficient to promote remyelination; and (ii) classifying the human as having a preselected level of remyelination. Optionally, the method can include the step of monitoring the human for remyelination. The method can also optionally include the step of identifying a human as one having, or at risk of developing, a demyelinating disorder or as one in need of, or likely to benefit from, increased remyelination. The demyelinating disorder can be any demyelinating disorder described herein (e.g., Multiple Sclerosis). The soluble LTβR can be any of those described herein. Administration of the soluble LTβR to a subject can include any of the routes, doses, or schedules described herein (e.g., see any of the administration methods described above). In some embodiments, the soluble LTβR (e.g., an LTβR fusion polypeptide such as LTβR-Fc) can be administered as a monotherapy or in combination with one or more additional therapies for a demyelinating disorder as described above. In some embodiments, the soluble LTβR can be administered to a subject receiving an anti-TNF therapy (e.g., Humira, Enbrel, or Remicade). Monitoring a subject (e.g., a human patient) for remyelination can include any of the methods described herein. Exemplary methods for classifying remyelination in a human (e.g., a patient) are described above.

In another aspect, the invention also provides a method of promoting remyelination. The method includes the steps of: (i) administering to a subject receiving an anti-TNF-therapy an effective dose of a soluble LTβR (e.g., an LTβR fusion polypeptide such as LTβR-Fc), and optionally, (ii) monitoring the human for remyelination. The method can also optionally include the step of identifying a subject as one having, or at risk of developing, a demyelinating disorder resulting from an anti-TNF therapy. The subject can be any subject described herein. Administration of the soluble LTβR to a subject can include any of the routes, doses, or schedules described herein (e.g., see any of the administration methods described above). In some embodiments, the soluble LTβR (e.g., an LTβR fusion polypeptide such as LTβR-Fc) can be administered as a monotherapy or in combination with one or more additional therapies for a demyelinating disorder as described above. In some embodiments, the anti-TNF therapy that the subject is receiving is, e.g., Humira, Enbrel, or Remicade. A subject can be identified as one having, or at risk of developing, a demyelinating disorder using any of the methods described herein. Monitoring a subject (e.g., a human patient) for remyelination can include any of the methods described herein (see the exemplary methods described above).

In another aspect, the invention features a method of selecting a patient as one in need of, or who could benefit from, administration of a soluble LTβR. The method includes the step of determining if a patient is in need of, or could benefit from, remyelination. The method can also include the step of treating the selected patient with a soluble form of LTβR. Methods for selecting the patient can include any of the methods exemplified herein including, for example, monitoring for one or more symptoms of a demyelinating disorder or any of the direct assessments of the state of myelin in a subject described above. The soluble LTβR can be any of those described herein. The dose, frequency of administration (i.e., schedule), and duration of treatment can be any of those described herein.

In some embodiments of the method, the patient is a patient diagnosed with a demyelinating disorder. In other embodiments of the method, the patient is one presenting one or more symptoms associated with a demyelinating disorder such as any of the symptoms described herein.

In another aspect, the invention provides a method of selecting a dose, route of administration, frequency of administration, and/or duration of treatment of a soluble LTβR to a patient. The method includes the steps of (i) evaluating the patient for one or more patient-specific factors and (ii) selecting a dose, frequency of administration, to and/or duration of treatment based on the assessment of the one or more factors, and (iii) optionally, where appropriate, administering to the patient a soluble LTβR at a dose, frequency of administration, and/or duration of treatment determined in step (ii). The method can also include the step of selecting a patient as one having, or at risk of developing, a demyelinating disorder. Accordingly, the patient can be one having, or likely to develop, a demyelinating disorder. The method can also include the step of monitoring the patient for remyelination following the treatment. The soluble LTβR can be any of those described herein.

In some embodiments, the patient can be determined not to be in need of, or likely to benefit from, administration of a soluble LTβR.

In another aspect, the invention provides a delivery device designed for intravenous, subcutaneous or intramuscular administration of a soluble LTβR (e.g., a LTβR fusion polypeptide such as LTβR-Fc) to a subject (e.g., a human (e.g., a human patient) having a demyelinating disorder, where the administration is sufficient such that remyelination occurs in the subject. The delivery device can be any suitable delivery device described herein including, for example, a syringe. The demyelinating disorder can be any demyelinating disorder described herein (e.g., Multiple Sclerosis). The subject can be any of the subjects described herein. The soluble LTβR can be any of the soluble LTβR polypeptides described herein.

In some embodiments, the delivery device contains a unit dose of a soluble LTβR (e.g., LTβR-Fc), where the unit dose is sufficient to increase remyelination.

Doses of about 0.001 mg/kg of a soluble LTβR are expected to be suitable starting points for optimizing treatment doses.

In some embodiments, the delivery device contains a lyophilized soluble LTβR (e.g., an LTβR fusion polypeptide such as LTβR-Fc).

In another aspect, the invention features a kit containing: (i) one or more unit doses of a soluble LTβR (e.g., a LTβR fusion polypeptide such as LTβR-Fc) and (ii) reagents and instructions for how to assay for remyelination. Instructions for how to assay for remyelination can include instructions for any of the methods for assessing remyelination described herein (see above).

In some embodiments, the kit is for the treatment of a demyelinating disorder (e.g., Multiple Sclerosis).

In another aspect, the invention features a delivery device containing two compartments, where the first compartment contains a unit dose of lyophilized soluble LTβR (e.g., an LTβR fusion polypeptide such as LTβR-Fc), wherein the unit dose is sufficient such that remyelination occurs in a subject (e.g., a human, e.g., a human patient); and the second compartment contains a liquid for reconstituting the soluble LTβR (e.g., an LTβR fusion polypeptide such as LTβR-Fc) prior to administration to the subject. The delivery device can be any suitable delivery device described herein including, for example, a syringe. The subject can be any of the subjects described herein. The soluble LTβR can be any of the soluble LTβR polypeptides described herein. The liquid can be any pharmaceutically acceptable diluent described herein, and can include, for example, a buffer (e.g., phosphate-buffered saline) or distilled and/or sterilized water.

In some embodiments, the delivery device contains a unit dose of a soluble LTβR (e.g., LTβR-Fc), such that administration of the reconstituted soluble LTβR (e.g., LTβR-Fc) to a subject will deliver to the subject at least about 0.001 mg of the soluble LTβR per kg body weight of the subject.

In another aspect, the invention provides a method of instructing a patient having a demyelinating disorder to treat the patient's demyelinating disorder, which includes the steps of: (i) providing the patient with at least two unit doses of a soluble LTβR (e.g., a LTβR-Fc); and (ii) instructing the patient to self-administer the unit doses subcutaneously, one dose at a time, wherein the unit dose of LTβR-Fc is sufficient to induce remyelination in a patient. Optionally, the method can include the step of instructing the patient to self-monitor for remyelination. The demyelinating disorder can be any of those described herein such as Multiple Sclerosis. The soluble LTβR can be any soluble LTβR polypeptide described herein such as the LTβR-Fc set forth in SEQ ID NO:1. Administration of one or more unit doses of a soluble LTβR (i.e., instructions for how to do so) can include any of the methods (e.g., schedules) described herein.

A "soluble LTβR," as defined herein, is a polypeptide that includes a lymphotoxin (LT)-binding fragment of the extracellular region of LTβR. For example, a soluble LTβR can include all or a fragment of the extracellular domain of human LTβR (e.g., it can include residues 40-200, 35-200, 40-210; 35-220, 32-225, or 28-225 of human LTβR as depicted by SEQ ID NO:2 below).

(SEQ ID NO: 2)
MLLPWATSAPGLAWGPLVLGLFGLLAASQPQAVPPYASENQTCRDQEKEY

YEPQHRICCSRCPPGTYVSAKCSRIRDTVCATCAENSYNEHWNYLTICQL

CRPCDPVMGLEEIAPCTSKRKTQCRCQPGMFCAAWALECTHCELLSDCPP

GTEAELKDEVGKGNNHCVPCKAGHFQNTSSPSARCQPHTRCENQGLVEAA

PGTAQSDTTCKNPLEPLPPEMSGTMLMLAVLLPLAFFLLLATVFSCIWKS

HPSLCRKLGSLLKRRPQGEGPNPVAGSWEPPKAHPYFPDLVQPLLPISGD

VSPVSTGLPAAPVLEAGVPQQQSPLDLTREPQLEPGEQSQVAHGTNGIHV

TGGSMTITGNIYIYNGPVLGGPPGPGDLPATPEPPYPIPEEGDPGPPGLS

TPHQEDGKAWHLAETEHCGATPSNRGPRNQFITHD.

In some embodiments, a soluble LTβR includes the extracellular region of the LTβR molecule as represented by residues 32-225 of SEQ ID NO:2 (depicted by SEQ ID NO:11 below).

(SEQ ID NO: 11)
AVPPYASENQTCRDQEKEYYEPQHRICCSRCPPGTYVSAKCSRIRDTVCA

TCAENSYNEHWNYLTICQLCRPCDPVMGLEEIAPCTSKRKTQCRCQPGMF

CAAWALECTHCELLSDCPPGTEAELKDEVGKGNNHCVPCKAGHFQNTSSP

SARCQPHTRCENQGLVEAAPGTAQSDTTCKNPLEPLPPEMSGTM.

In some embodiments, the full-length, immature LTβR R polypeptide is a full-length, immature LTβR polypeptide derived from any species (e.g., any mammal (e.g., a mouse, rat, or monkey) that expresses a homolog of human LTβR polypeptide as set forth in SEQ ID NO:2. In a preferred embodiment, the LTβR polypeptide is human LTβR.

In some embodiments, the LTBR moiety is itself soluble. In some embodiments, the LTBR is joined to a heterologous moiety that increases its solubility, e.g., an Fc region of an immunoglobulin molecule. In some embodiments, the heterologous moiety can be covalently joined to the LTBR moiety.

In some embodiments, a soluble LTβR can be modified by covalent attachment of a second polypeptide moiety, e.g., a heterologous polypeptide (e.g., to make an LTβR fusion protein) or a non-polypeptide moiety. In some cases, such moieties can improve a pharmacodynamic or pharmacokinetic parameter, such as solubility or half-life. LTβR fusion proteins can include all or part of the constant region of an antibody (e.g., an Fc domain), transferrin, or albumin, such as human serum albumin (HSA) or bovine serum albumin (BSA). The fusion protein can include a linker region between the LTβR sequence and the non-LTβR protein domain. In some embodiments, a soluble LTβR is modified by covalent attachment to a polymer such as a polyethylene glycol (PEG). While not limited by any particular theory or mechanism, such soluble LTβRs can act as decoy receptors to reduce (block) LTβR activity. An exemplary soluble LTβR is an LTβR-Fc, e.g., the LTβR-Fc having the sequence of SEQ ID NO:1 set forth below.

*M L L P W A T S A P G L A W G P L V L G L F G L L*

*A A* A V P P Y A S E N Q T C R D Q E K E Y Y E P Q

H R I C C S R C P P G T Y V S A K C S R I R D T V

C A T C A E N S Y N E H W N Y L T I C Q L C R P C

D P V M G L E E I A P C T S K R K T Q C R C Q P G

M F C A A W A L E C T H C E L L S D C P P G T E A

E L K D E V G K G N N H C V P C K A G H F Q N T S

S P S A R C Q P H T R C E N Q G L V E A A P G T A

Q S D T T C K N P L E P L P P E M S G T M V D K T

H T C P P C P A P E L L G G P S V F L F P P K P K

D T L M I S R T P E V T C V V V D V S H E D P E V

K F N W Y V D G V E V H N A K T K P R E E Q Y N S

T Y R V V S V L T V L H Q D W L N G K E Y K C K V

S N K A L P A P I E K T I S K A K G Q P R E P Q V

Y T L P P S R D E L T K N Q V S L T C L V K G F Y

P S D I A V E W E S N G Q P E N N Y K T T P P V L

D S D G S F F L Y S K L T V D K S R W Q Q G N V F

S C S V M H E A L H N H Y T Q K S L S L S P G

(Amino acids in italics indicate signal sequence; underlined amino acids indicate sequence derived from the extracellular region of LTβR; and amino acids in bold indicate IgG Fc sequence. A valine linking the LTβR sequence with the IgG-Fc sequence is artificial, and derived neither from the LTβR or the IgG-Fc sequence. The underlined sequence is a substantial part of the extracellular domain of LTβR and corresponds to amino acids 32 to 225 of SEQ ID NO:2 (see above)).

"Polypeptide" and "protein" are used interchangeably and mean any peptide-linked chain of amino acids, regardless of length or post-translational modification. The LTβR, heterologous polypeptides, or fusion proteins thereof, used in any of the methods of the invention can contain or be human proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required is that: (i) such variants of the soluble LTβR polypeptides have at least 25% (e.g., at least: 30%; 40%; 50%; 60%; 70%; 75%; 80%; 85%; 90%; 95%; 97%; 98%; 99%; 99.5%, or 100% or even greater) of the ability of the LTβR-Fc fusion protein (SEQ ID NO:1) to induce remyelination in a subject.

A "polypeptide fragment," as used herein, refers to a segment of the polypeptide that is shorter than a full-length, immature polypeptide. A "functional fragment" of a polypeptide has at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the activity of the mature, polypeptide. Fragments of a polypeptide include terminal as well as internal deletion variants of a polypeptide. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids.

Unless otherwise defined, all technical and scientific terms used herein have the same meaning as commonly understood by one of ordinary skill in the art to which this invention pertains. Preferred methods and materials are describe below, although methods and materials similar or equivalent to those described herein can be used in the practice or testing of the present invention. All publications, patent applications, patents, and other references mentioned herein are incorporated by reference in their entirety. The materials, methods, and examples disclosed herein are illustrative only and not intended to be limiting.

Other features and advantages of the invention will be apparent from the following description, from the drawings, and from the claims.

DESCRIPTION OF DRAWINGS

FIG. 5 is a graph depicting the severity of demyelination in wild-type C57BL6 mice following administration of hLtβR-Ig or human Ig control. On a scale depicting severity of demyelination, as assayed by LFB-PAS stained paraffin sections, 0 indicates normal myelination, and 3 indicates complete demyelination. Each circle represents an individual mouse: open circles, human-Ig treated mice; filled circles hLtβR-Ig treated mice. Horizontal lines indicate the median score of each group.

DETAILED DESCRIPTION

Figure 1:
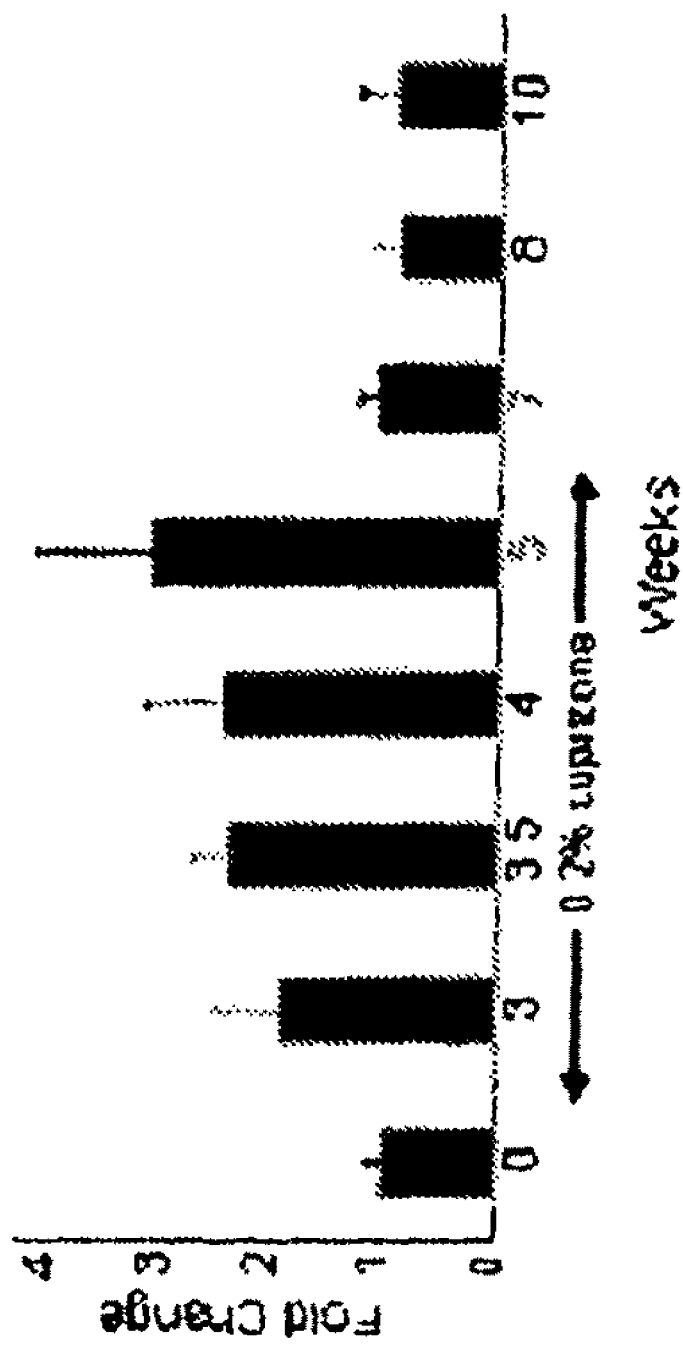
FIG. 1 is a graph depicting LTβR mRNA expression levels in wild-type mice during cuprizone treatment.

The soluble LtβRs described herein are lymphotoxin (LT) pathway inhibitors and are shown to promote remyelination. Thus, the soluble LtβRs can be useful for the treatment of demyelinating disorders. Demyelinating disorders can include, for example, Multiple Sclerosis (e.g., Relapsing/Remitting Multiple Sclerosis, Secondary Progressive Multiple Sclerosis, Progressive Relapsing Multiple Sclerosis, Primary Progressive Multiple Sclerosis, or Acute Fulminant Multiple Sclerosis), Central Pontine Myelinolysis, Acute Disseminated Encephalomyelitis, Progressive Multifocal Leukoencephalopathy; Subacute Sclerosing Panencephalitis, Post-infectious Encephalomyelitis, Chronic Inflammatory Demyelinating Polyneuropathy, Guillain-Barre Syndrome, Progressive Multifocal Leucoencephalopathy, Devic's Disease, Balo's Concentric Sclerosis, and a leukodystrophy (e.g., Metachromatic Leukodystrophy, Krabbé disease, Adrenoleukodystrophy, Pelizaeus-Merzbacher disease, Canavan disease, Childhood Ataxia with Central Hypomyelination, Alexander disease, or Refsum disease). The agents and methods described herein are particularly suitable for treatment of Multiple Sclerosis.

Multiple Sclerosis is an idiopathic disorder of the central nervous system in which the body's immune system attacks myelin in the brain and spinal cord. Whether the disease manifests in repeated episodes of inflammation or as a chronic condition, it often results in multiple scars (scleroses) on the myelin sheath, leading to impairment or loss of nerve function. Multiple Sclerosis, while primarily affecting young adults, can manifest in patients of any age. Symptoms of Multiple Sclerosis include, for example, impaired vision or cognitive function, numbness, weakness in extremities, tremors or spasticity, heat intolerance, speech impairment, incontinence, or impaired proprioception. Patients with Multiple Sclerosis often also present with depression.

Following administration of a soluble LTβR (e.g., LTβR-Fc)-containing composition to a subject (e.g., a human patient), the efficacy of the treatment (i.e., the remyelination resulting from the treatment) of a demyelinating disorder (e.g., Multiple Sclerosis) can be assessed, e.g., by comparing the extent of the patient's demyelinating disorder before and after treatment. Post-treatment assessment can occur immediately or shortly after treatment (e.g., one hour after treatment, two hours after treatment, three hours after treatment, six hours after treatment, 12 hours after treatment, or 18 hours after treatment) or can occur at least one day (e.g., at least one day, at least two days, at least three days, at least five days, at least a week, at least two weeks, at least three weeks, at least five weeks, at least two months, at least six months, or at least a year) following treatment. Where progression of the improvement of Multiple Sclerosis following one or more LTβR-Fc treatments (e.g., one or more treatments to induce remyelination) is to be assessed, a patient's symptoms or cognitive abilities can be evaluated or measured at multiple time points following LTβR-Fc treatment (e.g., a one day, two day, and one week evaluation; a one week, one month, and six month evaluation; a one month, six month, and one year evaluation). Progression of the improvement of a demyelinating disorder (e.g., Multiple Sclerosis) can also include measuring or assessing, for example, a change in the size or number of demyelinating lesions in a patient or a change (i.e., an improvement) in nerve function.

Suitable methods for evaluating the extent or severity of a demyelinating disorder (e.g., Multiple Sclerosis or any other demyelinating disorder described herein) are well known in the art. For example, the presence, extent, or severity of Multiple Sclerosis can be assessed in a patient through the use of a number of quantitative tests and evaluations. For example, a lumbar puncture (i.e., a spinal tap) can be performed on a patient to obtain a sample of cerebrospinal fluid. The cerebrospinal fluid is then tested for the presence of, e.g., (i) abnormal proteins such as tiny fragments of myelin, (ii) elevated levels of or specific types of lymphocytes, and/or (iii) abnormal levels of immunoglobulin (IgG) molecules. Another example of a quantitative test for a demyelinating disorder is an evoked potential test, which measures nerve activity as a function of how long it takes nerve impulses from the eye, ear, or skin to reach the brain. A demyelinating disorder can also be assessed by evaluating the size and/or number of inflammatory lesions (i.e., scleroses) present at the central nervous system using any of several methods of imaging including, but not limited to, Magnetic Resonance Imaging (MRI) scans, Positron-Emission Tomography (PET) scans, Diffusion-Weighted Imaging (DW-I, or DW-MRI), Diffusion Tensor Imaging, Myelography, Magnetization Transfer. Patients can also be diagnosed using a variety of semi-quantitative or qualitative assessments of their neuropsychology (e.g., the status of various abilities such as memory, arithmetic, attention, judgment and reasoning) or symptoms (clinical parameters) presented by the patient including, e.g., any of the symptoms of Multiple Sclerosis described above. Additionally, the extent or progression of a demyelinating disorder can be detected by testing a patient's urine for elevated levels of myelin basic protein-like material (MBPLM), which substance becomes elevated as axonal damage occurs during disease progression (see, for example, Whitaker et al. (1995) Ann. Neurol. 38(4):635-632). Certain tests for color blindness can also be helpful in tracking the effect of demyelinating disorders on the eyes.

Any of the diagnostic methods described above can also be used to evaluate increased remyelination in a subject (e.g., a patient) following treatment with a soluble LTβR (e.g., LTβR-Fc). For example, remyelination can coincide with a reduction in the size or number of scleroses present in a patient as determined through any of the imaging methods described herein. Also, remyelination in a subject could be measured as an increase in the speed of transmission of a signal from the ears, eyes, or skin to the brain, as determined through evoked potential testing. In some cases, remyelination can be evaluated as an increase in white matter volume (e.g., nerve mass of the spine or brain), particularly where the demyelinating disorder has resulted in nerve atrophy. In some instances, the extent or occurrence of remyelination a subject can be assessed by directly measuring the thickness of myelin in a subject using, e.g., magnetic resonance spectroscopy scans.

The efficacy of a given treatment (i.e., the extent of remyelination) in treating a demyelinating disorder (e.g., Multiple Sclerosis) can be defined as an improvement of one or more symptoms of demyelinating disorder (e.g., any of the symptoms described above) by at least 5% (e.g., at least 10%, at least 15%, at least 20%, at least 25%, at least 30%, at least 40%, at least 50%, at least 55%, at least 60%, at least 65% or more). In some cases, efficacy of a soluble LTβR (e.g., LTβR-Fc) treatment can be determined from the stabilization of one or more worsening symptoms associated with Multiple Sclerosis (i.e., the treatments curtail the worsening of one or more symptoms of Multiple Sclerosis). Treatment efficacy or extent of remyelination can also be evaluated in a patient using any of the diagnostic methods described herein, e.g., MRI or PET. For example, the amelioration of the size or number of demyelinating lesions (scleroses) following treatment with an LTβR-Fc can be monitored using MRI.

Combination Therapies

The methods and compositions described herein can be used in combination with other therapies used for the treatment of demyelinating disorders. For example, a soluble LTβR (e.g., LTβR-Fc) composition can be used in combination with direct therapies for Multiple Sclerosis such as, but not limited to, Interferon Beta 1a (Avonex), Interferon Beta 1b (Rebif), glatiramer acetate (Copaxone), mitoxantrone (Novantrone), azathiprine (Imuran), cyclophosphamide (Cytoxan or Neosar), cyclosporine (Sandimmune), methotrexate, Cladribine (Leustatin), methylprednisone (Depo-Medrol or Solu-Medrol), prednisone (Deltasone), prednisolone (Delta-Cortef), dexamethasone (Medrol or Decadron), adreno-corticotrophic hormone (ACTH), or Corticotropin (Acthar).

The methods and compositions (e.g., a soluble LTβR such as LTβR-Fc) provided herein can also be used in combination with therapies designed to treat the symptoms associated with a demyelinating disorder. Where the demyelinating disorder is Multiple Sclerosis, for example, a soluble LTβR (e.g., LTβR-Fc) can be administered in combination with one or more treatments for pain associated with Multiple Sclerosis including, e.g., carbamazepine, gabapentin, topiramate, zonisimide, phenytoin, pentoxifylline, ibuprofen, aspirin, or acetaminophen. A soluble LTβR (e.g., LTβR-Fc) can also be administered in combination with one or more treatments for anxiety or depression associated with Multiple Sclerosis including, e.g., fluoxetine, sertraline, vanlafaxine, citalopram, parocetine, trazodone, buproprion, diazepam, or amitriptyline.

Furthermore, a soluble LTβR (e.g., LTβR-Fc) can be administered in combination with one or more treatments for other symptoms of Multiple Sclerosis including, incontinence (e.g., oxybutynin, bethane, or imipramine), tremors or spasticity (e.g., baclofen, dantrolene sodium, or tizanidine), or vertigo (e.g., mecizine, dimenhydrinate, prochlorperazine, or scopolamine).

The present invention also includes the use of the methods and compositions described herein in combination with therapies or medicaments that can cause demyelinating conditions. For example, anti-TNF therapy for treatment of rheumatoid arthritis, as a side-effect, can result in a type of demyelinating condition. Thus, a soluble LTβR (e.g., LTβR-Fc) can be administered (e.g, co-administered) in combination with an anti-TNF therapy to prevent, ameliorate, or reverse the demyelination side-effects and to promote remyelination. Anti-TNF therapies include, but are not limited to, adalimumab (Humira), etanercept (Enbrel), or infliximab (Remicade).

Any of the methods or compositions described herein generally can be used in any circumstance where increasing remyelination would be advantageous.

In some instances, a soluble LTβR (e.g., LTβR-Fc) is used as a second line therapy. For example, a patient who is determined to be unresponsive to one or more therapies for a demyelinating disorder (e.g., Multiple Sclerosis) will stop receiving the one or more treatments and will begin treatment with a soluble LTβR, e.g., LTβR-Fc. Alternatively, the patient will continue to receive the one or more therapies for a demyelinating disorder while receiving treatment with the soluble LTβR.

Pharmaceutical Compositions

A soluble LTβR, e.g., LTβR-Fc, can be formulated as a pharmaceutical composition, e.g., for administration to a subject to treat a demyelinating disorder, such as Multiple Sclerosis. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge et al., J. Pharm. Sci. 66:1-19, 1977).

The soluble LTβR can be formulated according to standard methods. Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

In one embodiment, a soluble LTβR (e.g., LTβR-Fc) can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the soluble LTβR can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, cd., Marcel Dekker, Inc., New York, 1978.

A soluble LTβR (e.g., LTβR-Fc) can be modified, e.g., with a moiety that improves its stabilization and/or retention in circulation, e.g., in blood, serum, or other tissues, e.g., by at least 1.5, 2, 5, 10, or 50 fold. The modified agent can be evaluated to assess whether it can reach sites of inflammation (e.g., lesions or scleroses) such as can occur in a demyelinating disorder, such as Multiple Sclerosis (e.g., by using a labeled form of the agent).

For example, the soluble LTβR can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, a soluble LTβR can be conjugated to a water soluble polymer, e.g., a hydrophilic polyvinyl polymer, e.g., polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylcne (Pluronics); polymethacrylates; carbomers; and branched or unbranched polysaccharides.

When the soluble LTβR (e.g., LTβR-Fc) is used in combination with a second agent (e.g., any of the therapies for Multiple Sclerosis and other demyelinating disorders described herein), the two agents can be formulated separately or together. For example, the respective pharmaceutical compositions can be mixed, e.g., just prior to administration, and administered together or can be administered separately, e.g., at the same or different times.

Administration

A soluble LTβR (e.g., LTβR-Fc) can be administered to a subject, e.g., a human subject, by a variety of methods. For many applications, the route of administration is one of: intravenous injection or infusion (IV), subcutaneous injection (SC), intraperitoneally (IP), or intramuscular injection. In some cases, administration may be directly into the CNS, e.g., intrathecal, intracerebroventricular (ICV), intracerebral or intracranial. The agent can be administered as a fixed dose, or in a mg/kg dose.

The dose can also be chosen to reduce or avoid production of antibodies against the agent.

The route and/or mode of administration of the soluble LTβR can also be tailored for the individual case, e.g., by determining the location, number or size of scleroses in a subject, e.g., using Magnetic Resonance Imaging (MRI) scans, Positron-Emission Tomography (PET) scans, Diffusion-Weighted Imaging (DW-I, or DW-MRI), Diffusion Tensor Imaging, Myelography, Magnetization Transfer. The severity or extent of a demyelinating disorder can also be determined from lumbar puncture (e.g., to check for elevated white cells in the cerebral-spinal fluid), evoked potential testing as a measure of nerve function, and/or any other standard parameters associated with a demyelinating disorder (e.g., Multiple Sclerosis), e.g., any of the assessment criteria described herein.

Dosage regimens are adjusted to provide the desired response, e.g., a therapeutic response or a combinatorial therapeutic effect. The dosage regimen will, for example, cause an increase in remyelination. Generally, a dose of a soluble LTβR (e.g., LTβR-Fc) optionally formulated separately or together with an appropriate dose of a second therapeutic agent can be used to provide a subject with the soluble LTβR. Suitable dosages and/or dose ranges for the soluble LTβR include an amount sufficient to cause increased remyelination in a subject. Suitable dosages can be any of those described herein and include, for example, a dose of at least about 0.001 mg of a soluble LTβR per kg body weight of a subject (e.g., a human patient).

A dose of a soluble LTβR (e.g., an LTβR fusion polypeptide such as LTβR-Fc) required to increase remyelination can depend on a variety of factors including, for example, the age, sex, and weight of a subject to be treated. Other factors affecting the dose administered to the subject include, e.g., the type or severity of the demyelinating disorder. For example, a patient with Acute Fulminant Multiple Sclerosis may require a administration of a different dosage of a soluble LTβR than a patient with a milder form of Multiple Sclerosis. Other factors can include, e.g., other disorders concurrently or previously affecting the patient, the general health of the patient, the genetic disposition of the patient, diet, time of administration, rate of excretion, drug combination, and any other additional therapeutics that are administered to the patient. It should also be understood that a specific dosage and treatment regimen for any particular patient will depend upon the judgment of the treating physician. The amount of active ingredients will also depend upon the particular described compound and the presence or absence and the nature of the additional anti-viral agent in the composition.

Dosage unit form or "fixed dose" as used herein refers to physically discrete units suited as unitary dosages for the subjects to be treated; each unit contains a predetermined quantity of active compound calculated to produce the desired therapeutic effect (e.g., an crease in remyelination in a subject) in association with the required pharmaceutical carrier and optionally in association with the other agent. Suitable administration frequencies are described elsewhere herein.

A pharmaceutical composition may include a therapeutically effective amount of a soluble LTβR described herein. Such effective amounts can be determined based on the effect of the administered agent, or the combinatorial effect of an agent and secondary agent if more than one agent is used. A therapeutically effective amount of an agent can also vary according to factors such as the disease state, age, sex, and weight of the individual, and the ability of the compound to elicit a desired response in the individual, e.g., amelioration of at least one disorder parameter, e.g., amelioration of at least one symptom of a demyelinating disorder, e.g., Multiple Sclerosis. For example, a therapeutically effective amount of soluble LTβR will increase remyelination and can also slow and/or ameliorate demyelination. A therapeutically effective amount is also one in which any toxic or detrimental effects of the composition is outweighed by the therapeutically beneficial effects.

Devices and Kits

Pharmaceutical compositions that include a soluble LTβR (e.g., an LTβR-Fc) can be administered with a medical device. The device can be designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include a soluble LTβR, and can be configured to deliver one or more unit doses of the agent.

For example, the pharmaceutical composition can be administered with a transcutaneous delivery device, such as a syringe, including a hypodermic or multichamber syringe. Other suitable delivery devices include stents, catheters, transcutaneous patches, microneedles, and implantable controlled release devices.

The device (e.g., a syringe) can include a soluble LTβR in a dry or liquid form at a dose sufficient to cause remyelination. The device can also be a dual-chambered device, wherein one chamber contains a unit dose of lyophilized soluble LTβR (e.g., LTβR-Fc) sufficient to cause increased remyelination in a subject, and a second chamber containing a liquid (e.g., a buffer) for reconstituting the lyophilized unit dose of a soluble LTβR.

In other examples, the pharmaceutical composition can be administered with a needleless hypodermic injection device, such as the devices described in U.S. Pat. Nos. 5,399,163; 5,383,851; 5,312,335; 5,064,413; 4,941,880; 4,790,824; or 4,596,556. Examples of well-known implants and modules are described in, e.g., U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multichamber compartments; and U.S. Pat. No. 4,475,196, which discloses an osmotic drug delivery system. Many other devices, implants, delivery systems, and modules are also known.

A soluble LTβR (e.g., an LTβR-Fc) can be provided in a kit. In one embodiment, the kit includes (a) a container that contains a composition that includes one or more unit doses of a soluble LTβR, and optionally (b) informational material. The unit doses of soluble LTβR are sufficient to cause increased remyelination in a subject. The informational material can be descriptive, instructional, marketing or other material that relates to the methods described herein and/or the use of the agents for therapeutic benefit. The kit can also include reagents and instructions useful in the testing (assaying) for remyelination. Such methods of assaying for remyelination include, but are not limited to, any of the testing methods described herein. In one embodiment, the kit includes one or more additional agents for treating a demyelinating disorder, such as one or more agents to treat Multiple Sclerosis. For example, the kit includes a first container that contains a composition that includes the soluble LTβR, and a second container that includes the one or more additional agents.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the soluble LTβR (e.g., LTβR-Fc), e.g., in a suitable dose, dosage form, or mode of administration (e.g., a dose, dosage form, or mode of administration described herein), to treat a subject who has a demyelinating disorder, or who is at risk of developing, or for experiencing an episode associated with a demyelinating disorder. The information can be provided in a variety of formats, including printed text, computer readable material, video recording, or audio recording, or a information that provides a link or address to substantive material.

In addition to the agent, the composition in the kit can include other ingredients, such as a solvent or buffer, a stabilizer, or a preservative. The agent can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the soluble LTβR and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

Methods of Making Soluble LTBRs

Suitable methods of making soluble LTβRs are known in the art and are described, for example, in WO 97/03687, WO 98/17313, WO 00/21558, WO 99/38525, WO 00/36092. For example, an LTβR immunoglobulin fusion protein can be expressed in cell culture (e.g., mammalian cell culture (such as monkey COS cells or Chinese hamster ovary cells) or yeast cell culture) at a reduced temperature to produce an increased amount of properly folded fusion protein. The expressed fusion protein can be purified, e.g., by affinity or conventional chromatography techniques (see, e.g., WO 00/36092). All the above-mentioned PCT applications are incorporated herein by reference in their entirety.

The following examples are meant to illustrate, not limit, the invention.

EXAMPLES

Example 1

Materials and Methods

Animals. C57BL6 mice were purchased from Jackson Laboratories (Bar Harbor, Me.) and bred in house at the University of North Carolina (UNC) animal facility. LtβR$^{-/-}$ mice were bred in house at the UNC animal facility. All procedures were conducted in accordance with the National Institutes of Health (NIH) and were approved by the Institutional *Guide for the Care and Use of Laboratory Animals* Animal Care and Use Committee of UNC at Chapel Hill. All mice were at 8-10 weeks of age prior to the start of cuprizone treatment.

Treatment of mice. Male LtβR$^{-/-}$ and C57BL6 wild-type mice were fed ad libitum 0.2% cuprizone [oxalic bis(cyclohexylidenehydrazide)] (Aldrich, St. Louis, Mo.) mixed into milled chow. Mice were treated for 3, 3.5, 4, or 5 weeks to study the demyelination process. For remyelination, mice were returned to a diet of normal pellet chow for 1, 2 or 4 weeks following 6 full weeks of cuprizone treatment. Untreated mice were maintained on a diet of normal pellet chow.

Both human and mouse LtβR-Ig and their controls were kindly provided by Dr. J. Browning (Biogen Idec, Cambridge, Mass.) and are described in Gommerman et al. (2003) J. Clin. Invest. 112:755-767. To study demyelination, mice were pretreated on day-1 and weekly thereafter with intraperitoneal injections of 5 mg/kg of either human LtβR-human Ig (hLtβR-IgG-1 Fc) or human-Ig control. The post-treatment paradigm consisted of cuprizone treatment for 6 full weeks. After 5 weeks plus 2 days (approximate height of demyelination) of cuprizone treatment, mice were given intraperitoneal injections of either mouse LtβR-mouseIgG-1 or matched control MOPC-21 followed by weekly injections out to 10 weeks. This murine version of LtβR-Ig has been shown to be less antigenic in the mouse.

Tissue preparation and histopathological analysis. Paraffin-embedded coronal brain sections were prepared from the formix region of the corpus callosum. Luxol fast blue-periodic acid Schiff (LFB-PAS) stained sections were read by three double-blinded readers and graded on a scale from 0 (complete myelination) to 3 (complete demyelination), as described in Arnett et al. (2001) Nat. Neurosci. 4:1116-1122 and Plant et al. (2005) Glia 49:1-14.

Immunohistochemistry. Detection of mature oligodendrocytes, microglia/macrophages and astrocytes was performed by immunohistochemistry (Plant et al. (2005) Glia 49:1-14). Quantitative analyses of GSTπ and RCA-1 positive cells were restricted to a 0.033 mm$^2$ area at midline corpus callosum. Only immunopositive cells with an observable DAPI-stained nucleus were included in the quantification. Cell counts are averages of at least 9 and up to 14 mice per time point. Myelinated fibers were detected by immunohistochemistry with a primary antibody to myelin basic protein (Sternberger Monoclonals Inc. Lutherville, Md.) followed by flourescein-conjugated anti-mouse IgG (Invitrogen, Carlsbad, Calif.) diluted 1:1000.

In situ hybridization. Following cuprizone treatment, mice were perfused with RNase-free PBS and then 4% paraformaldehyde. Brains were removed and incubated in fixative until mounted for cryosectioning. Detection of mRNA for LtβR was performed by in situ hybridization as described in Schmid et al. (2002) J. Neurochem. 83:1309-1320.

RT-PCR and Quantitative Realtime RT-PCR. Total RNA was isolated from a dissected region of the brain containing the corpus callosum of wild-type and LtβR$^{-/-}$ mice at several points during and after cuprizone treatment. RNA isolation was performed using the Qiagen RNeasy kit under RNase-free conditions (Qiagen, Valencia, Calif.). RT-PCR for LIGHT was performed in 20 µl reactions using the following primers: 5' primer: CTGGCATGGAGAGTGTGGTA (SEQ ID NO:3); 3' primer: GATACGTCAAGCCCCTCAAG (SEQ ID NO:4).

TaqMan 5' nuclease quantitative real-time PCR assays were performed using an ABI Prism 7900 sequence-detection system (PE Applied Biosystems, Foster City, Calif.) in a 15 µl reaction with universal master mix (Invitrogen), 200 nM LtβR target primers, and 100 nM probe. LtβR specific primers were designed to span intron-exon junctions to differentiate between cDNA and genomic DNA. The primers and probe used to detect mouse LtβR were as follows: 5' primer, GTACTCTGCCAGCCTGGCACAGAAGC-CGAGGTCACAGATG (SEQ ID NO:5); 3' primer, GGTATGGGGTTGACAGCGGGCTCGAGGGGAGG (SEQ ID NO:6); probe, Fam-ACGTCAACTGTGTCCC-Tamra (SEQ ID NO:7). The primers and probe for mouse 18 S ribosomal RNA were 5' primer, GCTGCTGGCACCA-GACTT (SEQ ID NO:8); 3' primer, CGGCTACCACATC-CAAGG (SEQ ID NO:9); probe, Fam-CAAATTAC-CCACTCCCGACCCG-Tamra (SEQ ID NO:10). Thermal cycle parameters were optimized to 2 min at 50° C., 2 min at 95° C., and 40 cycles comprising denaturation at 95° C. for 15 sec and annealing-extension at 56° C. for 1.5 min. Reactions for 18 S were performed alongside LtβR during each experiment and used to normalize for amounts of cDNA.

Statistical analysis. Unpaired Student's t tests were used to statistically evaluate significant differences. Data are expressed as mean±s.e.m.

Example 2

LtβR Localization and Light Expression in the Brain

Ltα and Ltβ are found on a wide variety of haematopoietic cells while LtβR is expressed on dendritic cells and monocytes as well as most lineages of non-haematopoietic cells, follicular dendritic cells and high endothelial venules (Gommerman et al. (2003) Nat. Rev. Immunol. 3:642-655). Ltα and Ltβ have also been detected on astrocytes while LtβR has been detected on astrocytes and cells of monocytic origin (Cannella et al. (1997) J. Neuroimmunol. 78:172-179 and Plant et al. Glia 49:1-14). To assess LtβR expression in the cuprizone model, we performed quantitative real-time RT-PCR to examine the level of LtβR in the brains of untreated and cuprizone treated mice. Demyelination time points were obtained from mice treated for 3, 3.5, 4 or 5 weeks with cuprizone while remyelination time points were obtained from mice treated for 6 weeks and then released from cuprizone for 1, 2 or 4 weeks, corresponding to weeks 7, 8 and 10. Taqman probes specific for the LtβR gene and ribosomal 18S were used to detect transcripts in cDNA generated from brain RNA samples. As shown in FIG. 1, LtβR mRNA expression rose moderately in wild-type mice during cuprizone treatment (through week 6) (throughout the demyelination phase). LtβR mRNA expression levels declined to normal levels during the remyelination phase (weeks 7-10). Low levels of LtβR were detected in control untreated mice.

To define the cell type that expresses LtβR, in situ hybridization was used to localize LtβR in brains of untreated and cuprizone treated mice. LtβR was not expressed in brain prior to treatment. By 3 weeks of cuprizone treatment, a small amount of LtβR was detected in the corpus callosum region, however, by 5 weeks of treatment, a dramatic upregulation of LtβR was detected in this inflamed region. To determine which cell type expressed LtβR, in situ hybridization was coupled with immunohistochemical analysis. Microglia and macrophages were visualized in brain cyrosections using biotinylated tomato lectin, astrocytes Were visualized using GFAP-specific antibodies, oligodendrocytes using CNP-specific antibodies and neurons using NeuN-specific antibodies. LtβR expression could only be detected in lectin-positive cells. These results indicated that activated microglia and/or macrophages rather than astrocytes, oligodendrocytes or neurons express LtβR during cuprizone-induced inflammation and demyelination.

While not limited by any particular theory or mechanism, in view of previous findings that astrocytes are the source of Ltα (Plant et al. (2005) Glia 49:1-14), these data suggested that Ltαβ-LtβR signaling between astrocytes and microglia is primarily involved in the inflammatory demyelinating process that occurs during cuprizone treatment. In addition to Ltαβ, LtβR interacts with the membrane-bound ligand, LIGHT (homologous to lymphotoxins, exhibits inducible expression, and competes with herpes simplex virus glycoprotein D for the herpes-virus entry mediator (HVEM), a receptor expressed by T lymphocytes) (Granger et al. (2001) J. Clin. Invest. 108:1741-1742). LIGHT appears to be localized primarily to T cells, immature dendritic cells, granulocytes and monocytes (Gommerman et al. Nat. Rev. Immunol. 3:642-655), but has not been well-characterized in the brain. To determine if LIGHT expression was altered during cuprizone treatment, brain tissues were analyzed for LIGHT expression by RT-PCR. While LIGHT is found at high levels in the control spleen and thymus, extremely low to negligible levels were found in the brains of untreated or cuprizone treated mice. In addition, LIGHT was not regulated by the presence of LtβR as mice lacking LtβR express similar levels of LIGHT in the brain. While not limited by any particular theory or mechanism, these data suggested that LIGHT does not play a significant role during cuprizone-induced inflammation.

Example 3

Delayed Demyelination in LtβR$^{-/-}$ mice

The presence of Ltα exacerbated demyelination induced by cuprizone treatment (Plant et al. (2005) Glia 49:1-14).

Figure 2:
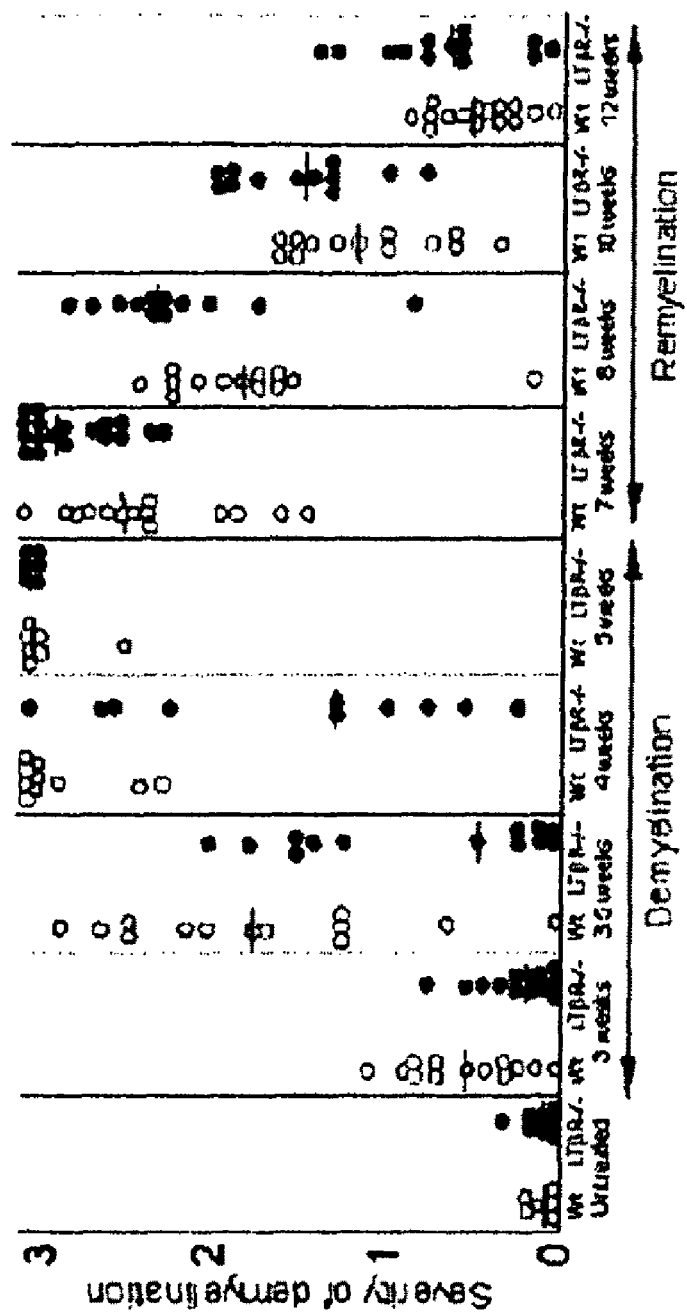
FIG. 2 is a graph depicting the severity of demyelination in LtβR$^{-/-}$ and wildtype mice. On a scale depicting severity of demyelination, as assayed by LFB-PAS stained paraffin sections, 0 indicates normal myelination, and 3 indicates complete demyelination. Each circle represents an individual mouse: open circles, C57BL6 wild-type (wt); filled circles, LtβR$^{-/-}$ mice. Horizontal lines indicate the median score of each group.

Furthermore, the lack of Ltα did not alter the course of remyelination nor the proliferation of oligodendrocyte progenitors following removal of cuprizone from the diet. Ltα can function as a homotrimeric molecule signaling through the TNF receptors, as well as a heterotrimeric molecule with Ltβ to signal through the LtβR. While the role of TNF receptors in the cuprizone model has been previously analyzed (Arnett et al. (2001) Nat. Neurosci. 4:1116-1122), the role of LtβR in this model was unknown. To analyze the role of LtβR, mice lacking this gene and wild-type controls were treated with 0.2% cuprizone in their diet for 3, 3.5, 4 or 5 weeks. Compared to wild-type mice, a significant delay in demyelination was exhibited by the LtβR$^{-/-}$ mice as assessed by LFB-PAS staining (FIG. 2). The LFB-PAS stained paraffin sections were assessed by three double-blind investigators. Significant differences in demyelination were seen between wt and LtBR$^{-/-}$ mice at 3 weeks ($p<0.02$), 3.5 weeks ($p<0.01$) and 4 weeks ($p<0.001$). While not limited by any particular theory or mechanism, these data indicated that signaling through LtβR exacerbates the inflammatory demyelinating process. This delay could be seen as early as 3 weeks ($p<0.02$) of cuprizone treatment but was most pronounced at 3.5 weeks ($p<0.01$) and 4 weeks ($p<0.001$) of treatment and is clearly revealed by representative LFB-PAS images of wild-type and LtβR$^{-/-}$ mice at 4 weeks of treatment. The delay in demyelination in LtβR$^{-/-}$ mice was similar to the delay in demyelination seen in Ltα$^{-/-}$ mice (Plant et al. (2005) Glia 49:1-14), therefore, while not limited by any particular theory or mechanism, these data suggested that membrane bound Ltαβ signaling through the LtβR is involved in the demyelination process.

Example 4

Delayed Remyelination in LtβR$^{-/-}$ Mice

The ability of mature oligodendrocytes to remyelinate the corpus callosum was studied in LFB-PAS stained paraffin sections from wild-type and LtβR$^{-/-}$ mice. Modest, but significant, differences in remyelination were observed between wild-type and LtβR$^{-/-}$ mice at 7 ($p<0.001$) and 10 weeks ($p<0.02$) (FIG. 2). By 12 weeks, LtβR$^{-/-}$ mice remyelinated to the same extent as wild-type controls ($p=0.11$). These differences during remyelination were less than 0.5 on our scale of severity of demyelination whereas differences seen in studies of TNFα$^{-/-}$ vs wild-type mice were greater than 1.5 on the scale (Arnett et al. (2001) Nat. Neurosci. 4:1116-1122), and persisted up to 14 weeks. While not limited by any particular theory or mechanism, while remyelination appeared to be delayed in LtβR$^{-/-}$ mice, it eventually resolved.

Example 5

Delayed Oligodendrocyte Loss in LtβR$^{-/-}$ Mice During Demyelination

To verify that the delay in demyelination observed by LFB-PAS was accompanied by changes in oligodendrocytes, immunohistochemistry was performed to detect mature oligodendrocytes in paraffin sections adjacent to those used for LFB staining. GSTπ+ was used as a marker for oligodendrocytes, and the cells at the midline corpus callosum were quantitated. In both wild-type and LtβR$^{-/-}$ mice, abundant oligodendrocytes were detected in untreated mice. However, after 3 and 3.5 weeks of treatment, more oligodendrocytes were detected in LtβR$^{-/-}$ mice compared to wild-type mice (3.5 weeks; $p<0.01$). No difference in oligodendrocyte numbers was found between wild-type and LtβR$^{-/-}$ mice at 4 weeks. These data were similar to the LFB staining results, except for the 4 week time point, where LFB staining showed reduced demyelination in the LtβR$^{-/-}$ mice. In contrast, GSTπ+ staining was not different between LtβR$^{-/-}$ and wild-type mice. While not limited by any particular theory or mechanism, the difference between GSTπ+ and LFB staining likely resulted from a delay between the disappearance of GSTπ+ cells and the actual loss of myelin. By 5 weeks of cuprizone treatment, few GSTπ+ oligodendrocytes were detected in the corpus callosum of wild-type and LtβR$^{-/-}$ mice. While not limited by any particular theory or mechanism, again, these data are consistent with the severe demyelination for both mouse strains.

Example 6

Figure 3:
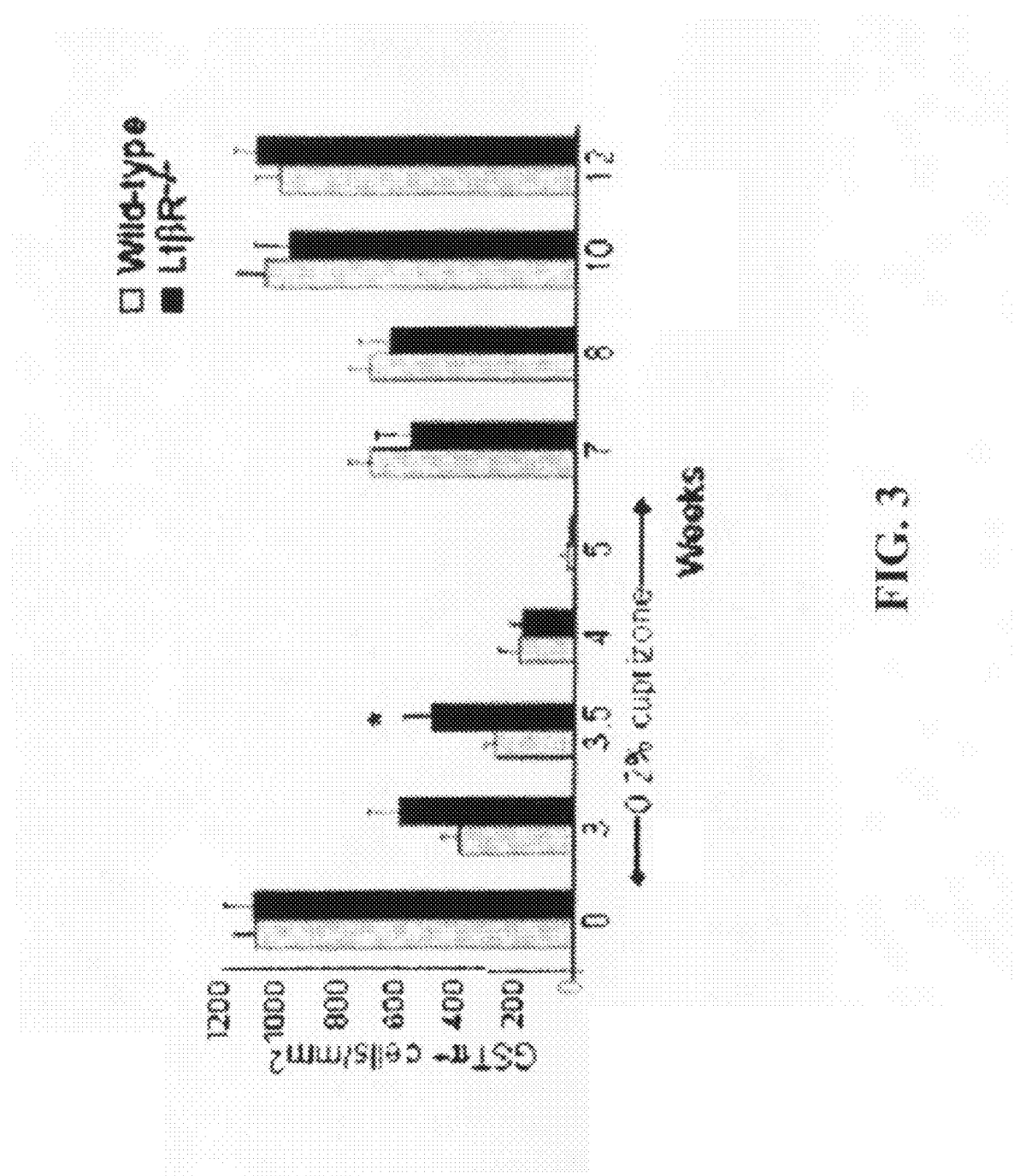
FIG. 3 is a graph depicting numbers of mature oligodendrocytes detected at the midline corpus callosum following treatment with cuprizone. Wild-type mice are indicated by gray bars; LtβR$^{-/-}$ mice are indicated by black bars.

Unchanged Oligodendrocyte Repopulation of Corpus Callosum in LtβR$^{-/-}$ Mice During the Remyelination Phase The involvement of LtβR in the reparative remyelination process was explored by examining paraffin sections at 7, 8, 10, and 12 weeks (1, 2, 4, and 6 weeks after the removal of cuprizone from the diet). To detect the presence of mature oligodendrocytes in the corpus callosum during the remyelination phase, immunohistochemistry using the GSTπ antibody was performed on paraffin sections from wild-type and LtβR$^{-/-}$ mice, followed by the quantitation of GSTπ positive cells. As shown in FIG. 3, more GSTπ+ cells were found in LtβR$^{-/-}$ mice compared to wild-type mice at 3 weeks ($p=0.09$), significantly more GSTπ+ cells were found in LtβR$^{-/-}$ mice at 3.5 weeks ($p<0.03$), and no differences in oligodendrocytes were found at 4 and 5 weeks of cuprizone treatment. After the removal of cuprizone, no differences in oligodendrocyte repopulation of the corpus callosum were observed between wild-type and LtβR$^{-/-}$ mice. Thus, even though rare oligodendrocytes were detected in these brains at the height of demyelination (5 weeks), just one week after the removal of cuprizone (7 weeks), the corpus callosum was repopulated to approximately 75% of its original numbers of mature oligodendrocytes. By week 10, the number of mature oligodendrocytes residing in the corpus callosum recovered to pretreatment levels in both wild-type and LtβR$^{-/-}$ mice. While not limited by any particular theory or mechanism, these data indicated that LtβR was not required for oligodendrocyte progenitor proliferation and maturation during the remyelination phase.

Example 7

Unaltered Microglia/Macrophage Recruitment in LtβR$^{-/-}$ Mice

Figure 4:
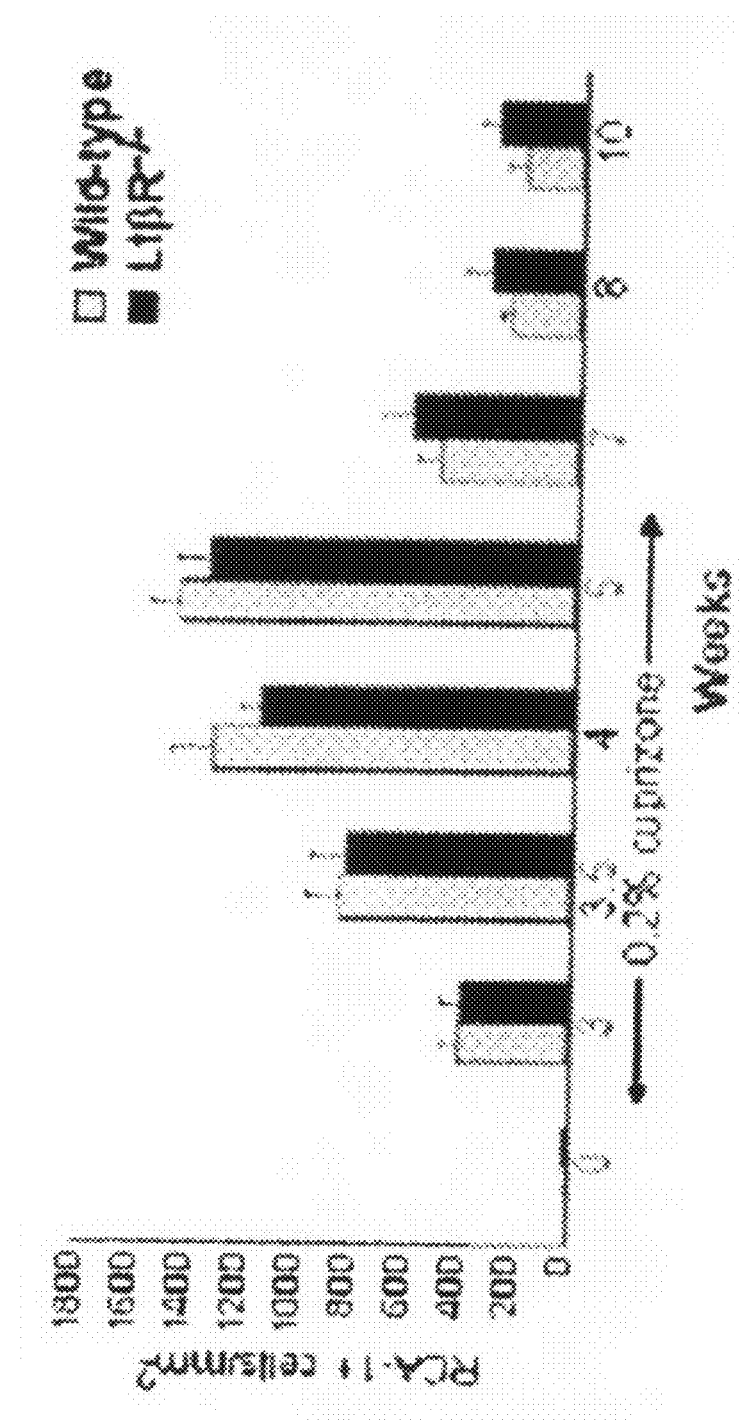
FIG. 4 is a graph depicting numbers of microglial/macrophage cells detected at the midline corpus callosum following treatment with cuprizone. Wild-type mice are indicated by gray bars; LtβR$^{-/-}$ mice are indicated by black bars.

Cuprizone induces a chronic inflammatory state in the brain including the recruitment of activated microglia and macrophages to the sites of insult (Matsushima et al. (2001) Brain Pathol. 11:107-116). Paraffin sections from LtβR$^{-/-}$ and wild-type mice were stained with the lectin RCA-1, and microglia/macrophages at midline corpus callosum were quantitated. As shown in FIG. 4, accumulation of microglia/macrophages at the midline corpus callosum was unaffected by the presence of LtβR. No significant differences in numbers of RCA-1+ cells were observed at any time point during the demyelination or remyelination phases of this model.

Example 8

Inhibition of Functional LtβR Reduces Demyelination

While not limited by any particular theory or mechanism, these studies suggested that LtβR had a dramatic exacerbating effect on demyelination, but a potentially modest beneficial effect during remyelination. However, mice lacking LtβR from birth have significant developmental problems. For example, LtβR$^{-/-}$ mice do not have mesenteric lymph nodes, Peyer's patches, and colon-associated lymphoid tissues and thus do not have a fully functioning immune system (Futterer et al. (1998) Immunity 9:59-70). In addition, it was known in the art that levels of chemokine and cytokine synthesis are controlled by LtβR (Chin et al. (2003) Immuno. Rev. 195: 190-201), but the full impact of LtβR control of chemokines and cytokines on the CNS is not known. Furthermore, natural killer cells in LtβR$^{-/-}$ mice do not have surface expression of the NK1.1 receptor due to the proximity of the encoding gene and the Ltbr gene (Wu et al. (2001) J. Immunol. 166:1684-1689).

Figure 5:
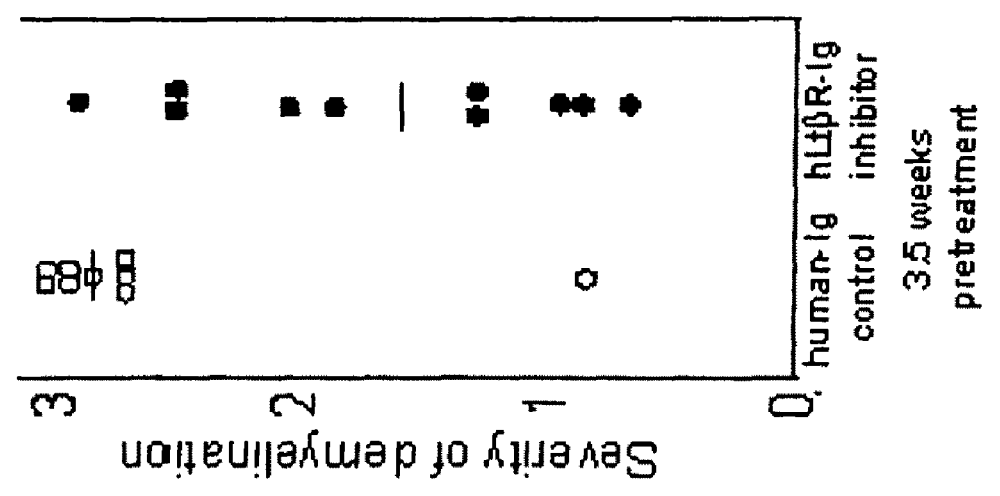

Functional inhibition of LtβR in wild-type mice was possible using a fusion decoy protein. To assess the validity of the aforementioned data in LtβR$^{-/-}$ mice, which demonstrated a detrimental role for LtβR during cuprizone-induced demyelination, C57BL6 mice were treated with either LtβR-Ig (human IgG$_1$ Fc, mouse LtβR) fusion decoy protein or polyclonal human IgG control during cuprizone treatment. Mice were pretreated on day-1 and weekly thereafter with intraperitoneal injections (5 mg/kg) and were maintained on an ad libitum diet of 0.2% cuprizone for 3.5 weeks. After 3.5 weeks, mice were perfused and paraffin brain sections were stained by the LFB-PAS method to assess the extent of demyelination at midline corpus callosum. Mice treated with human-Ig control were significantly more demyelinated than mice that received the LtβR-Ig inhibitor decoy protein (p<0.02) (FIG. 5). After 3.5 weeks, the average demyelination score of mice receiving control-Ig injections was very similar to wild-type mice treated for 4 weeks with cuprizone, while the average demyelination score of mice receiving injections of LtβR-Ig were very similar to LtβR$^{-/-}$ mice treated for 4 weeks with cuprizone. Immunohistochemistry for myelin basic protein (MBP) confirmed the lack of myelinated fibers in mice treated with human-Ig control compared to LtβR-Ig treated mice. In conclusion, these results suggested that demyelination in cuprizone-treated mice was significantly delayed by inhibition of the LtβR.

Example 9

Inhibition of LtβR Enhances Remyelination

Figure 6:
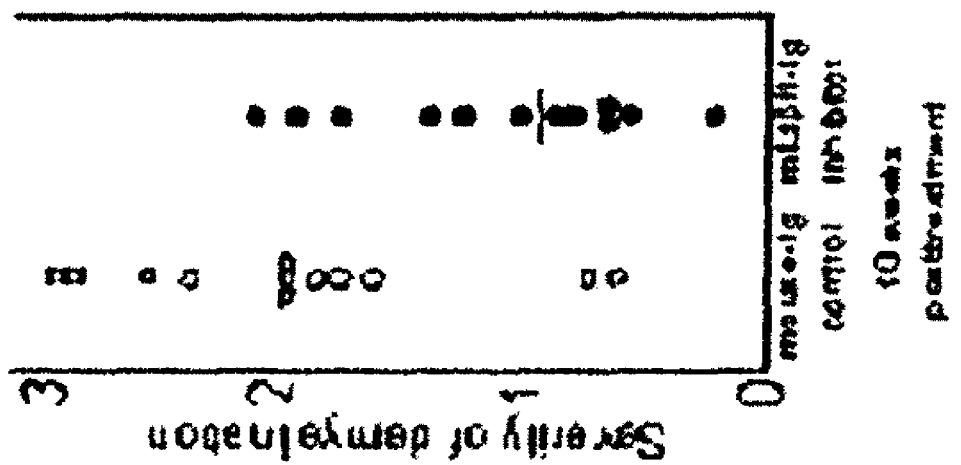
FIG. 6 is a graph depicting the severity of demyelination in wild-type C57BL6 mice following administration of mLtβR-Ig or mouse Ig control. On a scale depicting severity of demyelination, as assayed by LFB-PAS stained paraffin sections, 0 indicates normal myelination, and 3 indicates complete demyelination. Each circle represents an individual mouse: open circles, human-Ig treated mice; filled circles hLtβR-Ig treated mice. Horizontal lines indicate the median score of each group.

Next, the ability of the LtβR-IgG1 treatment to alter the extent of remyelination after significant demyelination had already occurred was examined. An advantage of the cuprizone model was the capacity to examine events that influence remyelination. To investigate the role of LtβR in the process of remyelination, C57BL6 mice were treated with 0.2% cuprizone for 6 weeks. This period of cuprizone treatment reproducibly resulted in complete demyelination in all mice studied to date, including the wildtype C57BL6 mice (Arnett et al. (2001) Nat. Neurosci. 4:1116-1122 and Plant et al. (2005) Glia 49:1-14). After 5 weeks plus 2 days of cuprizone treatment, mice were injected with either mouse LtβR-IgG-1 or control mouseIgG-1. This was followed by the weekly injection of either mouse LtβR-IgG1 or control mouse-IgG1 until week 10, when remyelination was clear. Due to the concern that human Fc might elicit an immune response in this prolonged experiment, a fusion protein consisting of mouse LtβR and mouse IgG1 Fc were used in this experiment. LFB stained sections were analyzed as above. Remarkably and surprisingly, mice treated with mLtβR-mIgG1 showed significantly more remyelination (p<0.007) than mice treated with the control-mIgG1 (FIG. 6). Additionally, immunohistocherriistry for MBP confirmed a reduced remyelination in mice treated with human-Ig control compared to LtβR-Ig treated mice. To verify these data, the number of mature oligodendrocytes within the corpus callosum at 10 weeks was quantitated. GSTπ positive oligodendrocytes were more abundant in the corpus callosum of mLtftR-IgG1 treated mice compared to control mouse-Ig treated controls (p<0.04). In conclusion, remyelination in cuprizone-treated mice was significantly enhanced by post-treatment with an inhibitor of LtβR signaling.

A number of embodiments of the invention have been described. Nevertheless, it will be understood that various modifications may be made without departing from the spirit and scope of the invention. Accordingly, other embodiments are within the scope of the following claims.

---

What is claimed is:

1. A method of treating a demyelinating disorder in a human, the method comprising
   (i) administering to a human an effective dose of a soluble Lymphotoxin-β-receptor (LTβR), and
   (ii) monitoring the human for remyelination.

2. The method of claim 1, wherein the soluble LTβR is administered to the human until remyelination is detected in the human.

3. The method of claim 1, wherein the dose is administered once every 3-10 days; at least twice and not more than once every 5-20 days; or at least twice and not more than every 28-31 days.

4. The method of claim 1, wherein the dose is administered weekly, biweekly or monthly.

5. The method of claim 1, wherein the dose is administered weekly over the course of at least 4 weeks.

6. The method of claim 1, wherein the soluble LTβR is human LTβR or an LT-binding fragment thereof.

7. The method of claim 6, wherein the soluble LTβR comprises an LT-binding fragment of the extracellular region of human LTβR (SEQ ID NO: 2) linked to an Fc region of an Ig.

8. The method of claim 7, wherein the soluble LTβR comprises the sequence set forth in SEQ ID NO:1.

9. The method of claim 1, wherein remyelination is monitored by an improvement of a symptom of a demyelinating disorder.

10. The method of claim 1, wherein the demyelinating disorder is Multiple Sclerosis.

11. The method of claim 1, wherein the demyelinating disorder is selected from the group consisting of Relapsing/Remitting Multiple Sclerosis, Secondary Progressive Multiple Sclerosis, Progressive Relapsing Multiple Sclerosis, Primary Progressive Multiple Sclerosis, and Acute Fulminant Multiple Sclerosis.

12. The method of claim 1, wherein the demyelinating disorder is selected from the group consisting of Central Pontine Myelinolysis, Acute Disseminated Encephalomyelitis, Progressive Multifocal Leukoencephalopathy; Subacute Sclerosing Panencephalitis, Post-infectious Encephalomyelitis, Chronic Inflammatory Demyelinating Polyneuropathy, Guillain-Barre Syndrome, Progressive Multifocal Leucoencephalopathy, Devic's Disease, Balo's Concentric Sclerosis, and a leukodystrophy.

13. A method of treating a demyelinating disorder in a human, the method comprising administering to a human a dose of a soluble LTβR, wherein the unit dosage, frequency of administration, and duration of treatment is sufficient such that remyelination occurs in the human.

14. A method of promoting remyelination, the method comprising:
   (i) administering to a human receiving an anti-TNF-therapy a dose of a soluble LTβR, and
   (ii) monitoring the human for remyelination.

15. The method of claim 14, wherein the human has an autoimmune disease.

16. The method of claim 15, wherein the autoimmune disease is rheumatoid arthritis.

17. The method of claim 14, wherein the soluble LTβR is administered to the human until remyelination is detected in the human.

18. The method of claim 14, wherein the soluble LTβR is human LTβR or a LT-binding fragment thereof.

19. The method of claim 14, wherein the dose is administered once every 3-10 days; at least twice and not more than once every 5-20 days; or at least twice and not more than once every 28-31 days.

20. The method of claim 14, wherein the dose is administered weekly, biweekly or monthly.

21. The method of claim 14, wherein the dose is administered weekly over the course of at least 4 weeks.

22. The method of claim 18, wherein the soluble LTβR comprises a substantial portion of the extracellular region of human LTβR (SEQ ID NO: 2) linked to an Fc region of an Ig.

23. The method of claim 22, wherein the soluble LTβR comprises the sequence set forth in SEQ ID NO:1.

24. The method of claim 14, wherein remyelination is monitored by an improvement of a symptom of a demyelinating disorder.

25. The method of claim 24, wherein the symptom is impaired vision, numbness, weakness in extremities, tremors, heat intolerance, speech impairment, incontinence, or impaired proprioception.

26. A delivery device designed for subcutaneous or intramuscular administration of a dose of soluble LTβR sufficient to promote remyelination, to a human having a demyelinating disorder.

27. The delivery device of claim 26, wherein the delivery device is used to deliver lyophilized soluble LTBR.

28. The delivery device of claim 26, wherein the soluble LTβR is human LTβR or an LT-binding fragment thereof.

29. The delivery device of claim 28, wherein the soluble LTβR comprises a substantial portion of the extracellular region of human LTβR (SEQ ID NO: 2) linked to an Fc region of an Ig.

30. The delivery device of claim 29, wherein the soluble LTβR comprises the sequence set forth in SEQ ID NO:1.

31. The delivery device of claim 26, wherein the delivery device is a syringe.

32. The delivery device of claim 26, wherein the demyelinating disorder is Multiple Sclerosis.

* * * * *